United States Patent
Su et al.

(10) Patent No.: US 10,993,923 B2
(45) Date of Patent: May 4, 2021

(54) METHOD FOR AMELIORATING FIBROSIS USING 1-[4-CHLORO-3-(TRIFLUOROMETHYL) PHENYL]-3-[3-(4-CYANOPHENOXY) PHENYL]UREA

(71) Applicants: Kuen-Feng Chen, Taipei (TW); Chung-Wai Shiau, Taipei (TW)

(72) Inventors: Tung-Hung Su, Taipei (TW); Kuen-Feng Chen, Taipei (TW); Chung-Wai Shiau, Taipei (TW); Cheng-Yi Wang, Taipei (TW)

(73) Assignees: Kuen-Feng Chen, Taipei (TW); Chung-Wai Shiau, Taipei (TW)

( * ) Notice: Subject to any disclaimer, the term of this patent is extended or adjusted under 35 U.S.C. 154(b) by 0 days.

(21) Appl. No.: 16/335,504

(22) PCT Filed: Sep. 22, 2017

(86) PCT No.: PCT/CN2017/102945
§ 371 (c)(1),
(2) Date: Mar. 21, 2019

(87) PCT Pub. No.: WO2018/054354
PCT Pub. Date: Mar. 29, 2018

(65) Prior Publication Data
US 2020/0016100 A1 Jan. 16, 2020

Related U.S. Application Data

(60) Provisional application No. 62/398,274, filed on Sep. 22, 2016.

(51) Int. Cl.
*A61K 31/17* (2006.01)
*A61P 1/16* (2006.01)

(52) U.S. Cl.
CPC ............... *A61K 31/17* (2013.01); *A61P 1/16* (2018.01)

(58) Field of Classification Search
None
See application file for complete search history.

(56) References Cited

FOREIGN PATENT DOCUMENTS

| CN | 102406641 A | 4/2012 |
|---|---|---|
| WO | WO2013020014 A1 | 2/2013 |
| WO | WO2017036405 A1 | 3/2017 |

OTHER PUBLICATIONS

Chinese Patent Publication CN102406641A English translation, downloaded from Espacnet.com on May 15, 2020, 28 pages.*
Su, T.H. et al., "Src-homology protein tyrosine phosphatase-1 agonist, SC-43, reduces liver fibrosis", Scientific Reports, 7 (1), May 11, 2017, p. 1-11.
Su, T.H. et al., "Sorafenib and its derivative SC-1 exhibit antifibrotic effects through signal transducer and activator of transcription 3 inhibition", Proceedings of the National Academy of Sciences of the United States of America, 112(23), Jun. 9, 2015, p. 7243-7248.
Tai, W. T. et al., "Discovery of Novel Src Homology Region 2 Domain-Containing Phosphatase 1 Agonists From Sorafenib for the Treatment of Hepatocellular Carcinoma", HEPATOLOGY, vol. 59, No. 1, Jan. 31, 2014, p. 190-201.

* cited by examiner

*Primary Examiner* — Savitha M Rao
*Assistant Examiner* — Gregg Polansky
(74) *Attorney, Agent, or Firm* — WPAT, PC

(57) ABSTRACT

The present invention provides an application of 1-[4-chloro-3-(trifluoromethyl)phenyl]-3-[3-(4-cyanophenoxy)phenyl]urea in preparation of drugs for treating and reducing a fibrotic disease. The fibrotic disease is skin sclerosis, cardiac fibrosis, pulmonary fibrosis, hepatic fibrosis, pancreatic fibrosis, or renal fibrosis.

2 Claims, 51 Drawing Sheets

METHOD FOR AMELIORATING FIBROSIS USING 1-[4-CHLORO-3-(TRIFLUOROMETHYL) PHENYL]-3-[3-(4-CYANOPHENOXY) PHENYL]UREA

CROSS-REFERENCE TO RELATED APPLICATION

This application claims priority of U.S. provisional application No. 62/398,274, filed on Sep. 22, 2016 the content of which is incorporated herein in its entirety by reference.

BACKGROUND OF THE INVENTION

1. Field of the Invention

The present invention relates to a method of using 1-[4-chloro-3-(trifluoromethyl)phenyl]-3-[3-(4-cyanophenoxy) phenyl]urea for ameliorating fibrosis.

2. The Prior Art

Fibrosis is a pathological change, which is characterized by the initiation of proliferation of fibroblasts, the increase of fibrous connective tissue in tissues and organs, and the decrease of parenchymal cells, and the continuous progression leading to tissue and organ structural damage and loss of function. Fibrosis of vital organs seriously affects the quality of life of patients and even life-threatening. Fibrotic diseases include diseases involving multiple systems, such as systemic sclerosis, multifocal fibrosis, scleroderma, renal multi-system fibrosis, and organ-specific diseases such as skin, heart, lung, liver, kidney fibrosis, etc. The causes of different fibrotic diseases are different, such as tissue and organ damage, infection, immune response, chronic inflammation, etc., but their common feature is the excessive deposition of extracellular matrix (ECM) in tissues and organ tissue remodeling.

Hepatic fibrosis refers to the pathological process of abnormal proliferation of connective tissue in the liver caused by various pathogenic factors and excessive precipitation of diffuse extracellular matrix in the liver. A variety of factors can cause liver fibrosis, such as viral infections, inflammatory reactions and alcohol abuse, etc. The pathological features of hepatic fibrosis are massive fibrous tissue hyperplasia and deposition in the hepatic portal vein and hepatic lobule, but no interlobular septa has been formed. The cirrhosis has pseudolobule formation, and the central venous region and the hepatic portal vein are separated. The normal structure is destroyed, and the hepatic fibrosis is further developed as cirrhosis.

Pulmonary fibrosis diseases include idiopathic pulmonary fibrosis, sarcoidosis, hypersensitivity pneumonitis, pneumoconiosis, fibrosis caused by drugs and radiation, and fibrotic alveolitis associated with collagen vascular disease, which are a wide range of diseases spectrum. The main pathological features include proliferation of lung mesenchymal cells, deposition of extracellular matrix and remodeling of lung parenchyma. At present, anti-inflammatory, anti-oxidation, anti-fibroblast proliferation, anti-collagen deposition, and lung transplantation are mainly used to treat pulmonary fibrosis. As the most common type of interstitial lung disease, idiopathic pulmonary fibrosis (IPF) is a progressive and generally fatal disorder of unknown etiology that predominantly occurs in middle-aged and elderly adults. Although the widely accepted clinical presentation of IPF consists of varying degrees of interstitial fibrosis and parenchymal inflammation, additional diagnostically relevant findings remain largely elusive. IPF is characterized by the loss of respiratory function with marked distortion of lung architecture. The histopathological hallmarks of patients with IPF are known as fibroblast foci, which consist of aggregates of activated fibroblasts that produce excessive levels of extracellular matrix (ECM) within the alveolar space at the site of epithelial cell loss.

Since lung fibroblasts play an important role in ECM deposition in pulmonary fibrosis, the origin of the expanded populations of these cells in the lungs is of substantial interest. There is one classic theory and one contemporary theory for the origin of fibroblasts/myofibroblasts. The classic concept is that tissue injury induces the activation of a resident fibroblast to proliferate and express constituents of the ECM. The contemporary theory is that tissue injury with the presence of TGF-β induces the transition of epithelial cells to a mesenchymal phenotype, the fibroblast/myofibroblast, that subsequently contributes to fibroproliferation and fibrosis. Therefore, the inactivation of fibroblast and the suppression of epithelial to mesenchymal transition (EMT) will be important to ameliorate pulmonary fibrosis.

SUMMARY OF THE INVENTION

To solve the foregoing problem, one objective of the present invention is to provide a method of ameliorating a fibrotic disease, comprising administering to a subject in need thereof a therapeutically effective amount of 1-[4-chloro-3-(trifluoromethyl)phenyl]-3-[3-(4-cyanophenoxy) phenyl]urea.

Another objective of the present invention is to provide a method of treating a disease characterized by the inactivation of the SRC homology region 2-containing tyrosine phosphatase-1, comprising administering to a subject in need thereof a therapeutically effective amount of 1-[4-chloro-3-(trifluoromethyl)phenyl]-3-[3-(4-cyanophenoxy) phenyl]urea which is named SC-43.

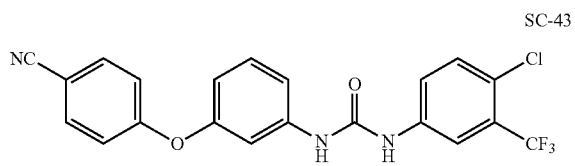 [SMILES: N#Cc1ccc(Oc2cccc(NC(=O)Nc3ccc(Cl)c(C(F)(F)F)c3)c2)cc1]

The other objective of the present invention is to provide method of treating a disease characterized by the inactivation of the SRC homology region 2-containing tyrosine phosphatase-1, comprising administering to a subject in need thereof a therapeutically effective amount of 1-[4-chloro-3-(trifluoromethyl)phenyl]-3-[3-(4-cyanophenoxy) phenyl]urea.

In one embodiment of the present invention, 1-[4-chloro-3-(trifluoromethyl)phenyl]-3-[3-(4-cyanophenoxy)phenyl] urea increases the activity of an SRC homology region 2-containing tyrosine phosphatase-1.

In one embodiment of the present invention, the disease characterized by the inactivation of the SRC homology region 2-containing tyrosine phosphatase-1 is a fibrotic disease.

In one embodiment of the present invention, the fibrotic disease is skin sclerosis, cardiac fibrosis, pulmonary fibrosis, hepatic fibrosis, pancreatic fibrosis, or renal fibrosis.

The embodiments of the present invention evaluate the effect of anti-fibrosis of cells or animals given 1-[4-chloro- 3-(trifluoromethyl)phenyl]-3-[3-(4-cyanophenoxy)phenyl]
urea by observing the SHP-1/STAT3 signaling pathway of
the hepatic fibrosis and pulmonary fibrosis The 1-[4-chloro-
3-(trifluoromethyl)-phenyl]-3-[3-(4-cyanophenoxy)phenyl]
urea compound, activates SHP-1 by directly interacting with
the inhibitory N—SH$_2$ domain and the catalytic tyrosine
phosphatase domain to promote the fibroblast apoptosis to
exhibit the anti-fibrotic activity thereof.

The embodiments of the present invention are further
described with the drawings. The following embodiments
are given to illustrate the present invention and are not
intended to limit the scope of the present invention, and
those having ordinary skill in the art can make some
modifications and refinements without departing from the
spirit and scope of the present invention. Therefore, the
scope of the present invention is defined by the scope of the
appended claims.

phenyl]urea induces apoptosis of hepatic stellate cells via the increased cleavage of poly(ADP-ribose) polymerase (PARP) fragments; n=3-4 for each group.

Figure 14A:
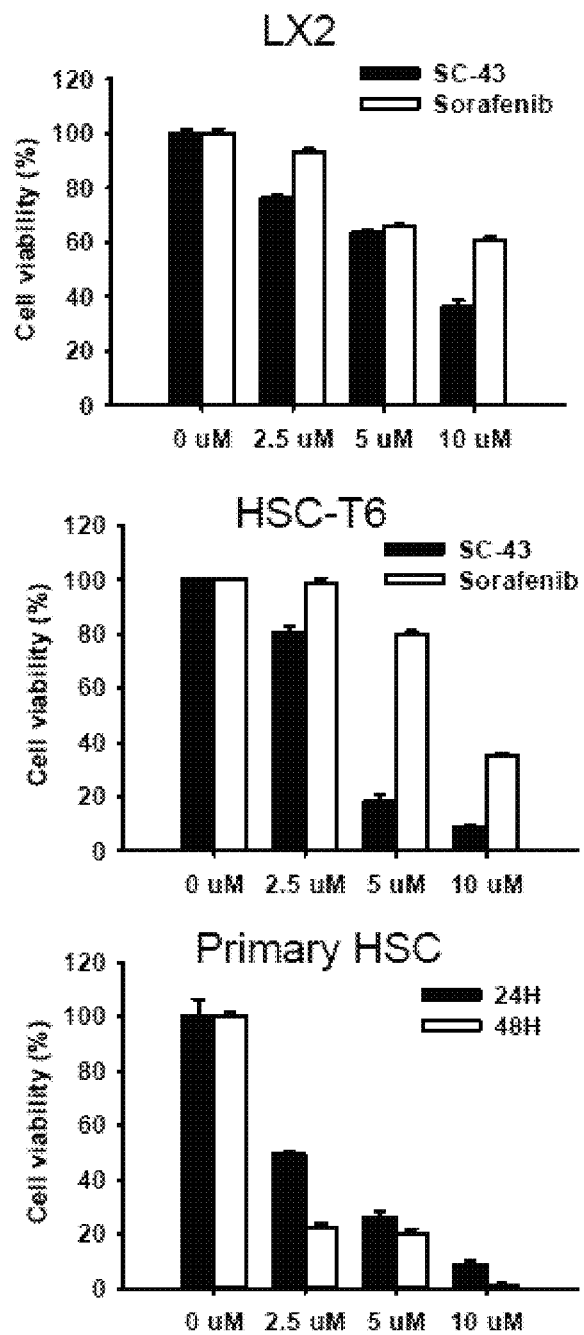
FIG. 14A shows the survival rate of hepatic stellate cells given 1-[4-chloro-3-(trifluoromethyl)phenyl]-3-[3-(4-cyanophenoxy)phenyl]urea under the time-and-dose-dependent manner; giving 1-[4-chloro-3-(trifluoromethyl)phenyl]-3-[3-(4-cyanophenoxy)phenyl]urea or sorafenib in HSC-T6 cells and LX2 cells for 24 hours; giving 1-[4-chloro-3-(trifluoromethyl)phenyl]-3-[3-(4-cyanophenoxy)phenyl]-urea in primary mouse HSCs cells for 24 or 48 hours respectively; the column represents the mean, and the error bar represents the standard deviation; n=3-4 for each group.
Figure 14B:
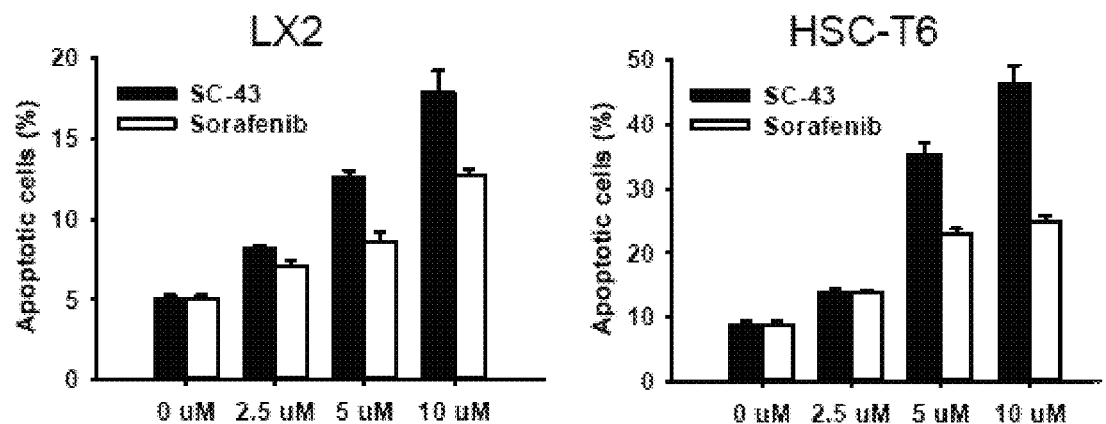
FIG. 14B shows the apoptosis of hepatic stellate cells given 1-[4-chloro-3-(trifluoromethyl)phenyl]-3-[3-(4-cyanophenoxy)phenyl]urea under the time-and-dose-dependent manner; giving 1-[4-chloro-3-(trifluoromethyl)phenyl]-3-[3-(4-cyanophenoxy)phenyl]urea or sorafenib in HSC-T6 cells and LX2 cells for 24 hours. The column represents the mean, and the error bar represents the standard deviation; n=3-4 for each group.
Figure 14C:
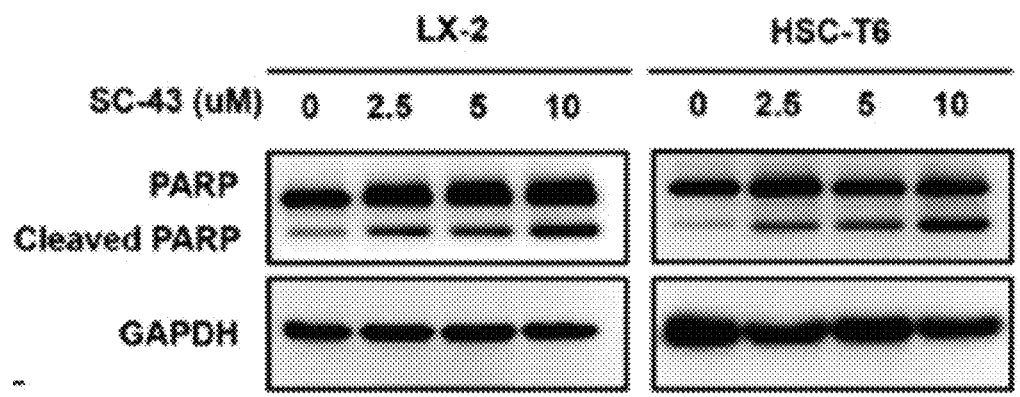
FIG. 14C shows the gel electropherogram of that 1-[4-chloro-3-(trifluoromethyl)phenyl]-3-[3-(4-cyanophenoxy)
Figure 14D:
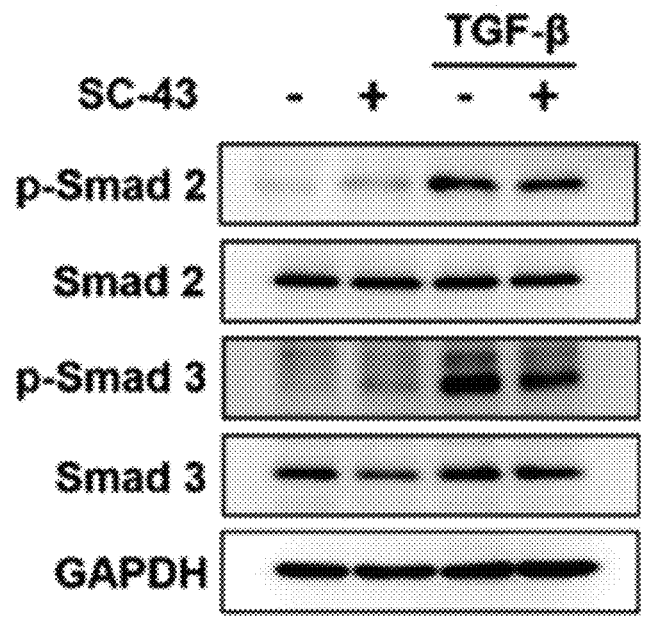

FIG. 14D shows the gel electropherogram of that 1-[4-chloro-3-(trifluoromethyl)phenyl]-3-[3-(4-cyanophenoxy)phenyl]urea induces the downregulation of the transforming growth factor (TGF)-beta pathway p-Smad2 and p-Smad3 in LX2 cells; n=3-4 for each group.

Figure 14E:
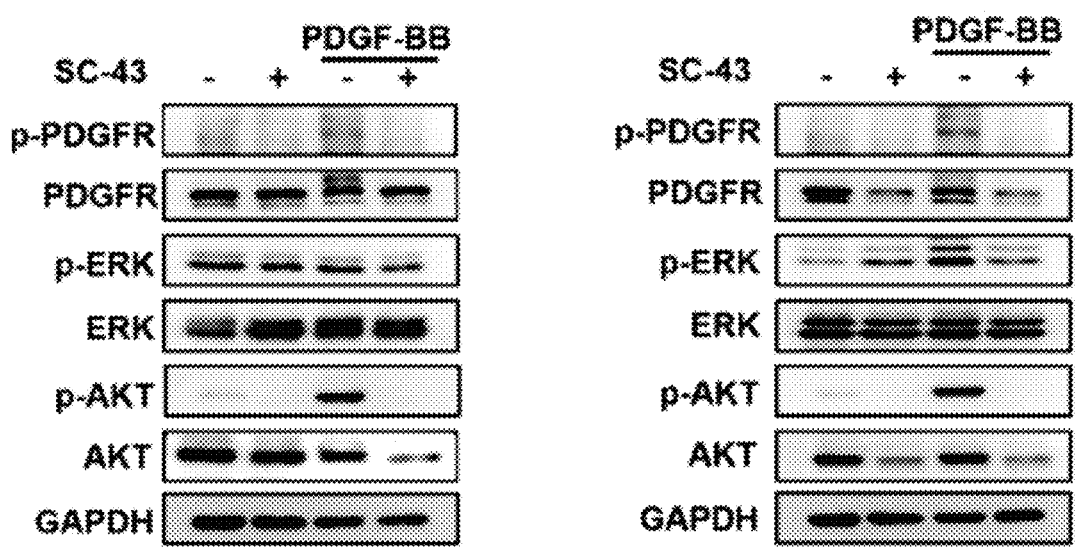

FIG. 14E shows the gel electropherogram of that 1-[4-chloro-3-(trifluoromethyl)phenyl]-3-[3-(4-cyanophenoxy)phenyl]urea induces the downregulation of the platelet-derived growth factor receptor (PDGFR) pathway p-PDGFR and p-Akt in LX2 and HSC-T6 cells; n=3-4 for each group.

Figure 15A:
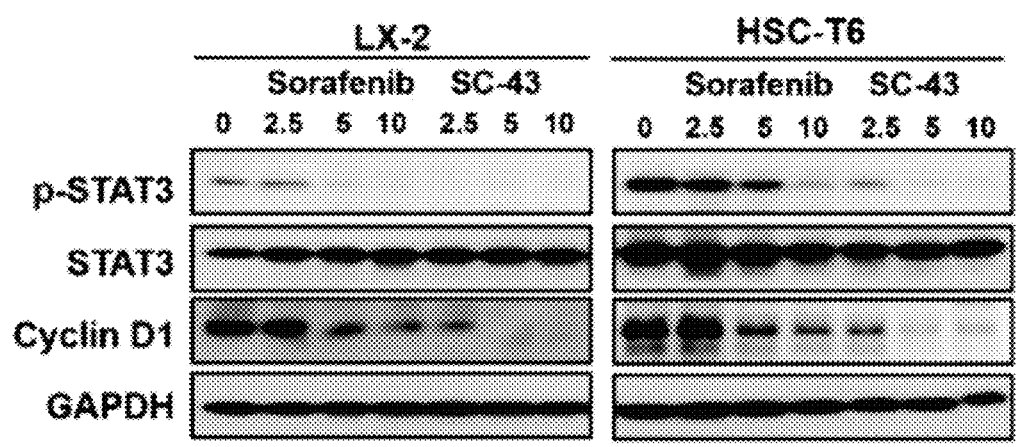

FIG. 15A shows the gel electropherogram of the dose-dependent down-regulation of p-STAT3 and cyclin D1 by 1-[4-chloro-3-(trifluoromethyl)-phenyl]-3-[3-(4-cyanophenoxy)phenyl]urea treatment in LX2 and HSC-T6 cells.

Figure 15B:
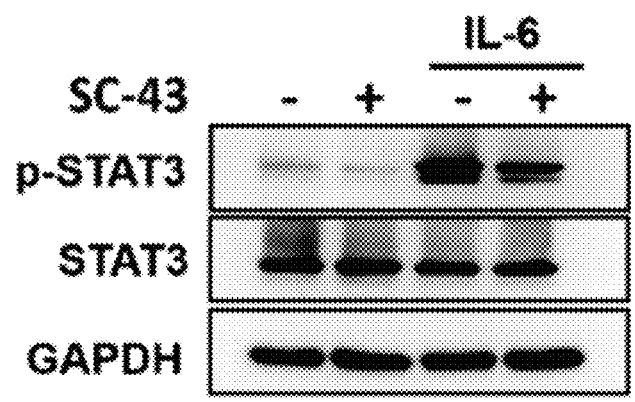

FIG. 15B shows the gel electropherogram of that 1-[4-chloro-3-(trifluoromethyl)phenyl]-3-[3-(4-cyanophenoxy)phenyl]urea down-regulates interleukin (IL)-6-STAT3.

Figure 15C:
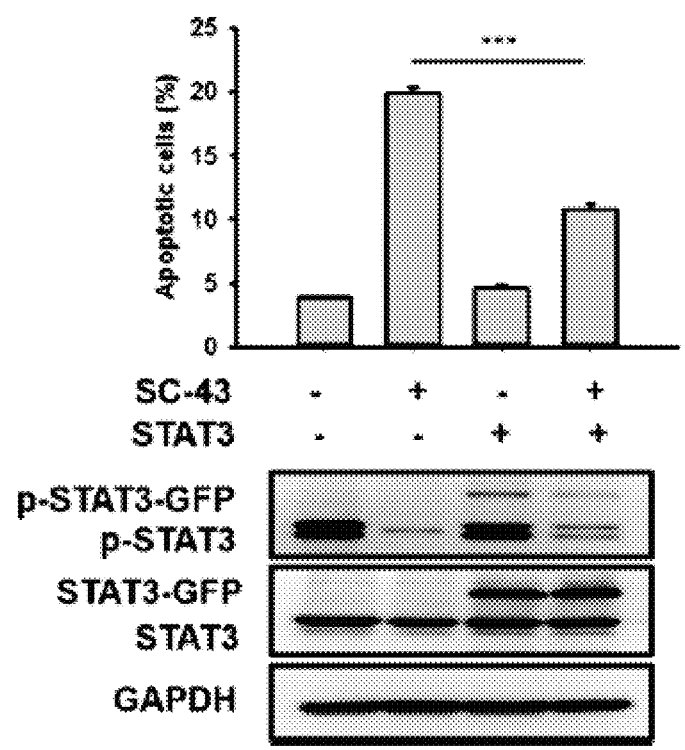

FIG. 15C shows the over-expression of STAT-3 significantly offsets the 1-[4-chloro-3-(trifluoromethyl)phenyl]-3-[3-(4-cyanophenoxy)phenyl]urea-induced apoptosis in HSC; the column represents the mean, and the error bar represents the standard deviation; ***P<0.001 compared to vehicle.

Figure 15D:
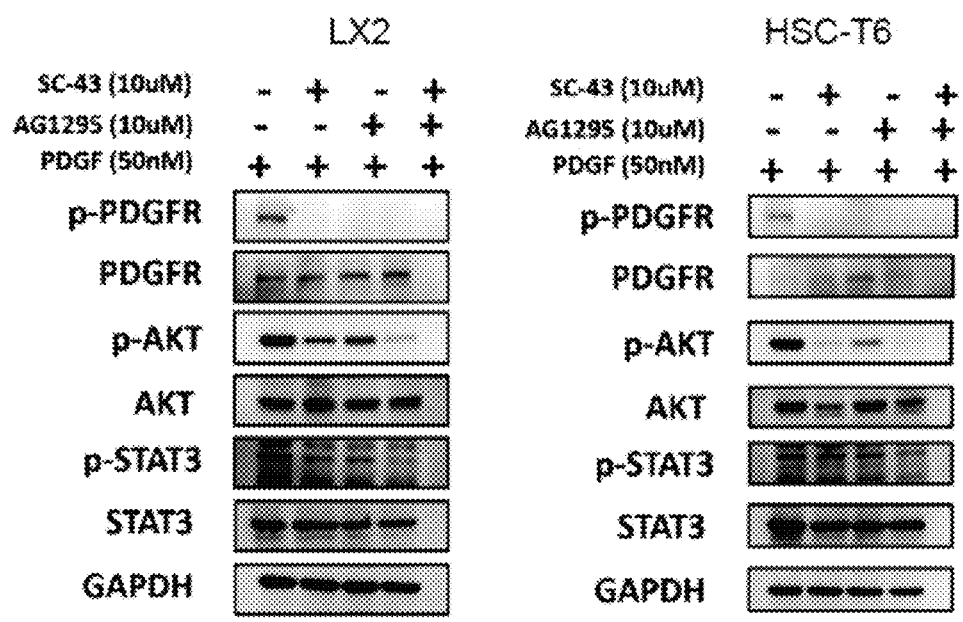

FIG. 15D shows 1-[4-chloro-3-(trifluoromethyl)phenyl]-3-[3-(4-cyanophenoxy)phenyl]urea down-regulates the p-Akt and p-STAT3 after giving the specific PDGFR inhibitor AG1295.

Figure 16A:
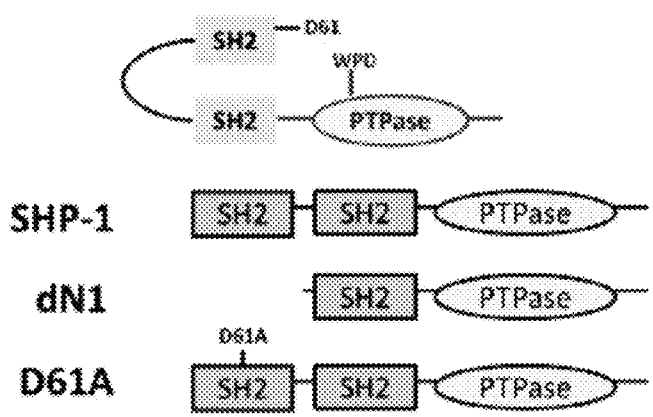

FIG. 16A shows the schematic diagram of SHP-1, its mutant dN1 (containing the N—SH$_2$ domain deletion), and D61A (single mutation from D61).

Figure 16B:
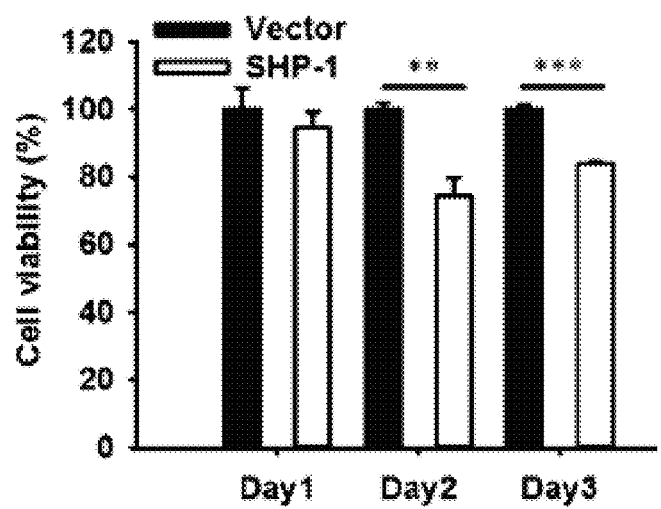

FIG. 16B shows the over-expression of SHP-1 significantly reduces the survival rate of LX2 cells; the column represents the mean, and the error bar represents the standard deviation; *P<0.05, P<0.01, and *P<0.001, and n=3-5 for each group.

Figure 16C:
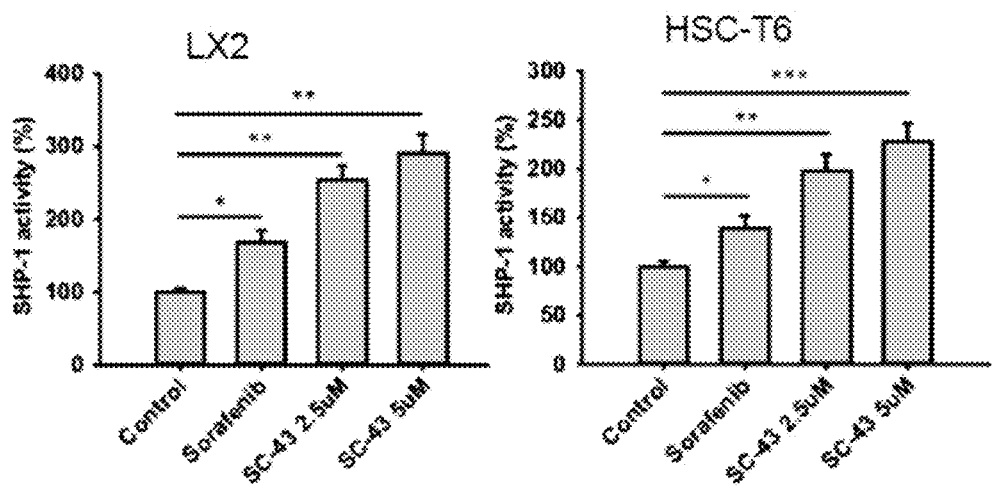

FIG. 16C shows that after giving sorafenib (5 μM) or 1-[4-chloro-3-(trifluoromethyl)phenyl]-3-[3-(4-cyanophenoxy)phenyl]urea (2.5 or 5 μM) in LX2 and HSC-T6 cells increases the activity of SHP-1 to increase the apoptosis rate; the column represents the mean, and the error bar represents the standard deviation; *P<0.05, P<0.01, and *P<0.001, and n=3-5 for each group.

Figure 16D:
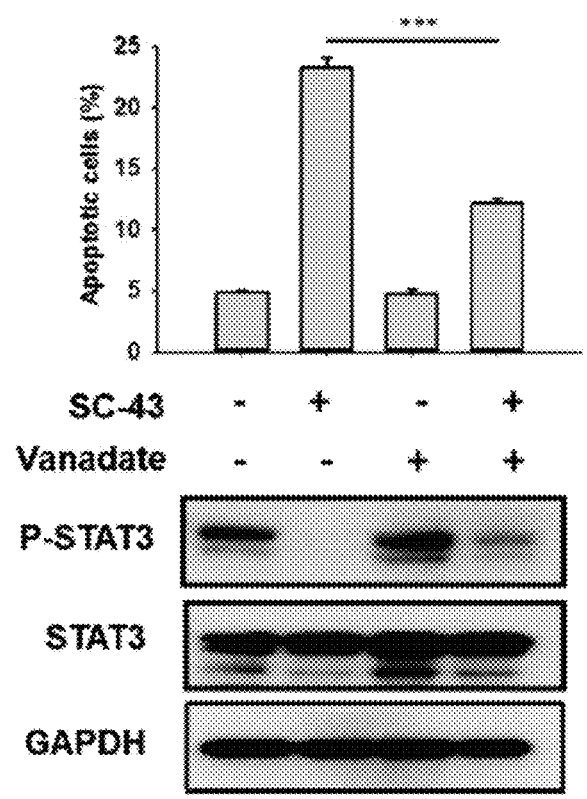

FIG. 16D shows the non-specific phosphatase inhibitor vanadate up-regulates p-STAT3 and reduces apoptosis; the column represents the mean, and the error bar represents the standard deviation; *P<0.05, P<0.01, and *P<0.001, and n=3-5 for each group.

Figure 16E:
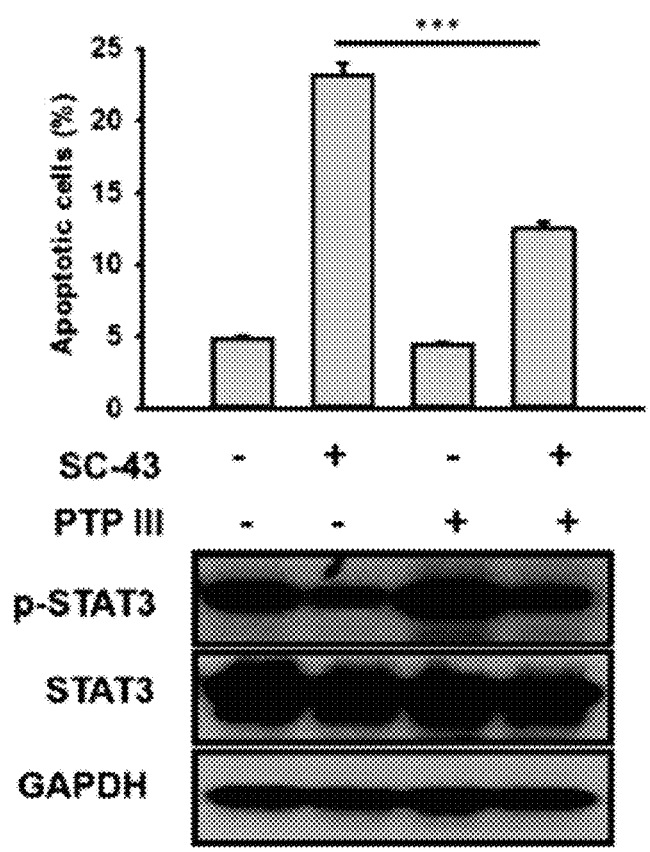

FIG. 16E shows the SHP-1 specific inhibitor (PTP inhibitor III) up-regulates p-STAT3 and reduces the apoptosis; the column represents the mean, and the error bar represents the standard deviation; *P<0.05, P<0.01, and *P<0.001, and n=3-5 for each group.

Figure 16F:
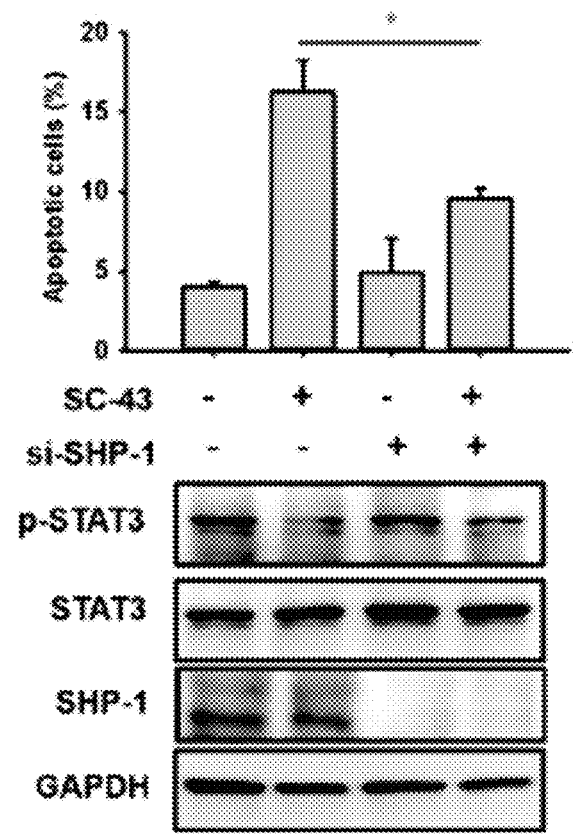

FIG. 16F shows siRNA silence SHP-1 gene to reverse the effect of 1-[4-chloro-3-(trifluoromethyl)phenyl]-3-[3-(4-cyanophenoxy)phenyl]urea on p-STAT and apoptosis; the column represents the mean, and the error bar represents the standard deviation; *P<0.05, P<0.01, and *P<0.001, and n=3-5 for each group.

Figure 17A:
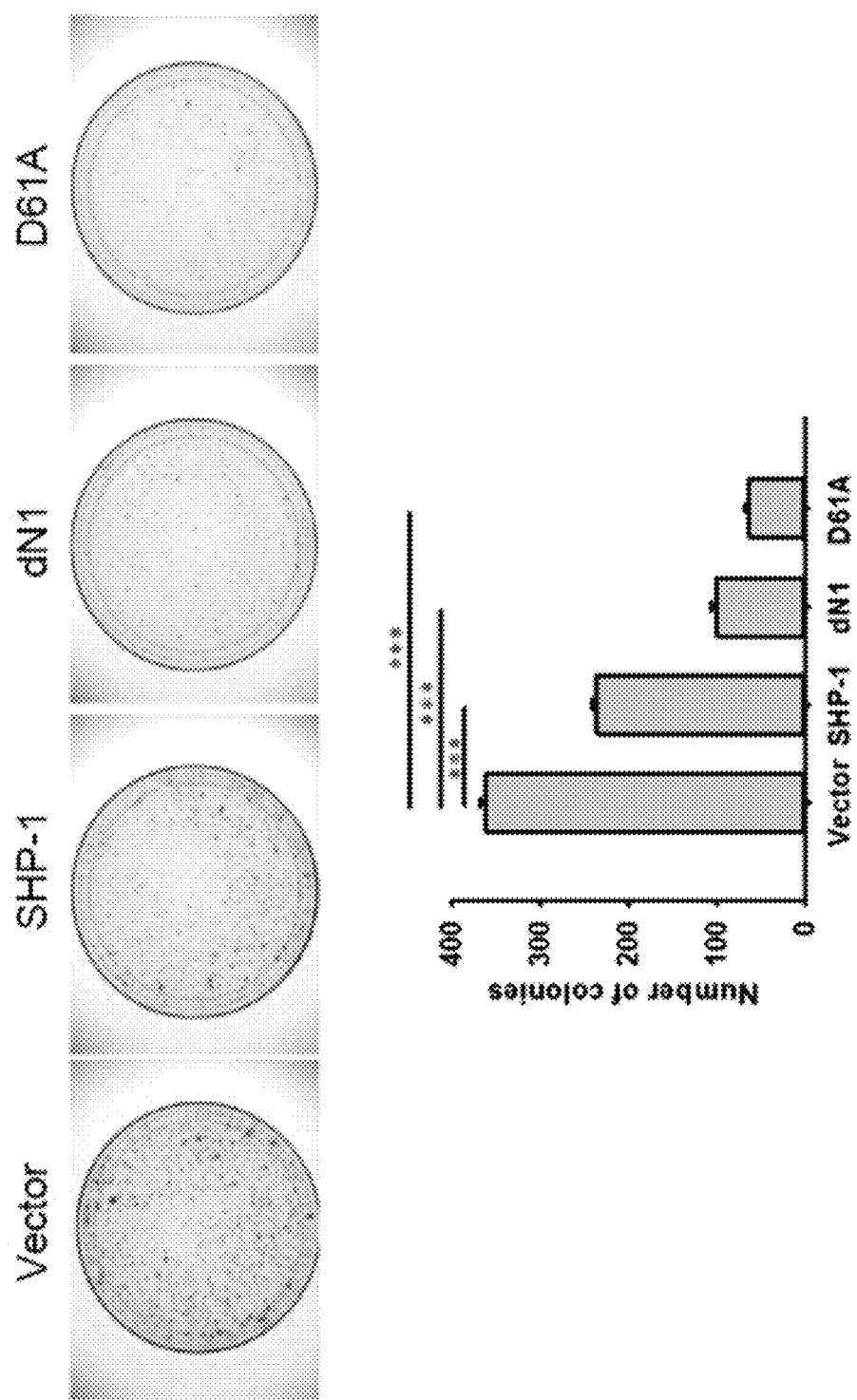

FIG. 17A shows the ectopic expressions of SHP-1, dN1, and D61A mutant significantly inhibit the formation of cell colonies; the column represents the mean, and the error bar represents the standard deviation; ***P<0.001, and n=3-5 for each group.

Figure 17B:
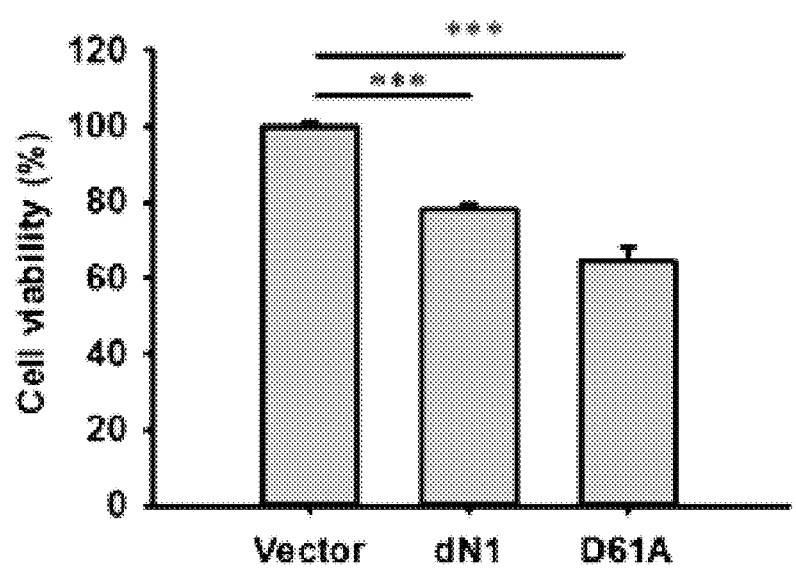

FIG. 17B shows the ectopic expressions of dN1 and D61A mutant significantly reduce the survival rate of cells; the column represents the mean, and the error bar represents the standard deviation; ***P<0.001, and n=3-5 for each group.

Figure 17C:
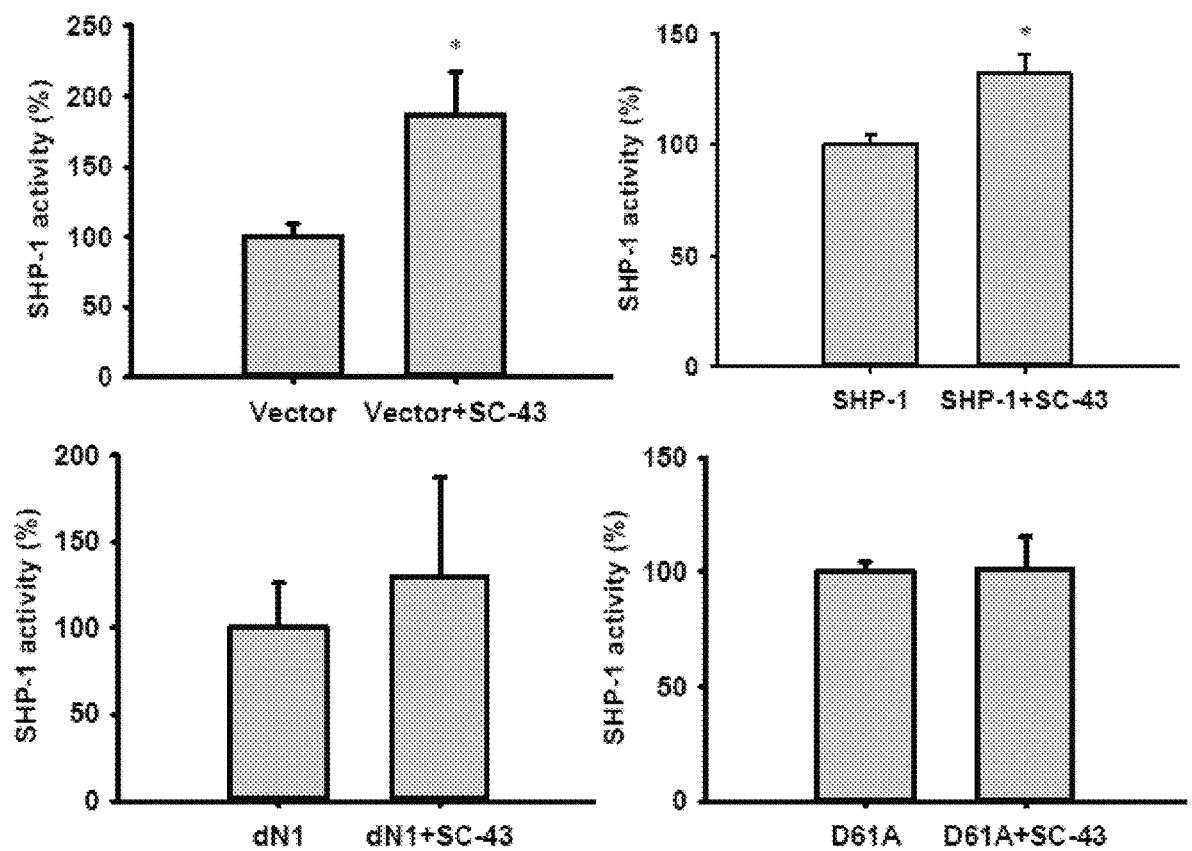

FIG. 17C shows 1-[4-chloro-3-(trifluoromethyl)phenyl]-3-[3-(4-cyanophenoxy)phenyl]urea significantly increases the activity of the vector and wild-type SHP-1 but does not increase the activity of dN1 and D61A mutant; the column represents the mean, and the error bar represents the standard deviation; *P<0.05, and n=3-5 for each group.

Figure 17D:
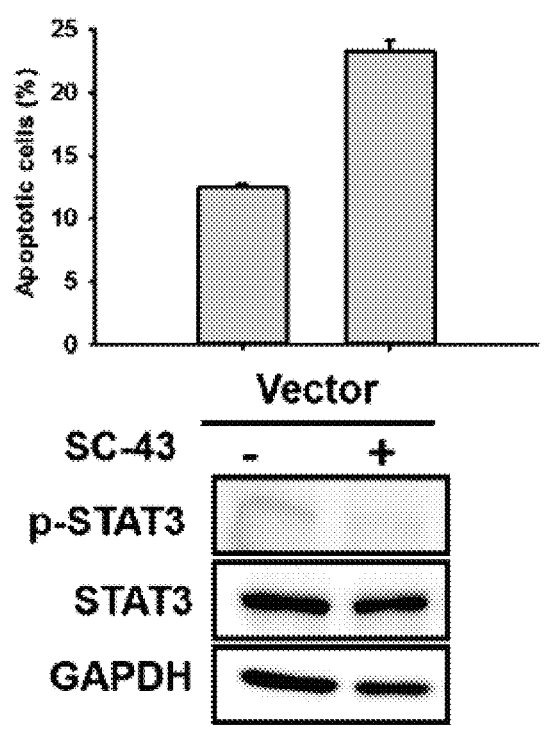

FIG. 17D shows after treated with 1-[4-chloro-3-(trifluoromethyl)phenyl]-3-[3-(4-cyanophenoxy)phenyl]urea (5 μM, 24 hours), the ectopic expressions of the control vector and the wild-type SHP-1 significantly increase the apoptosis of LX2 cells and down-regulate p-STAT3; column represents the mean, and the error bar represents the standard deviation, and n=3-5 for each group.

Figure 17E:
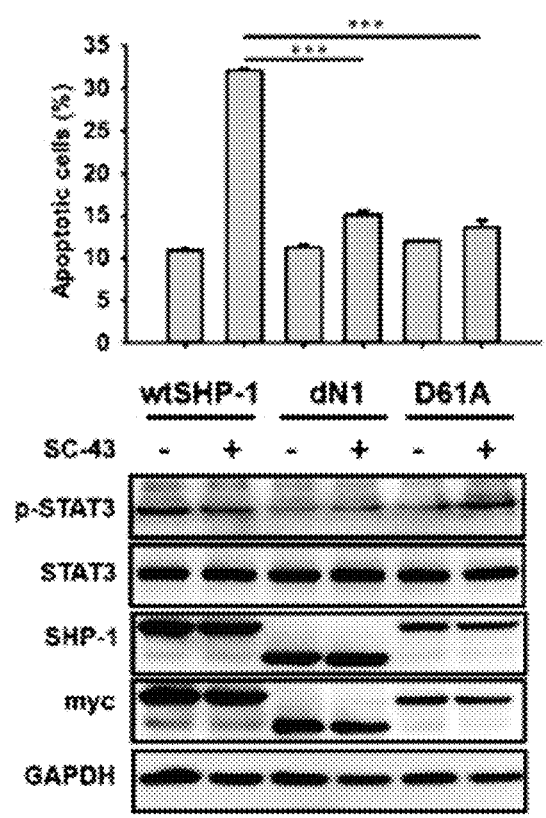

FIG. 17E shows 1-[4-chloro-3-(trifluoromethyl)phenyl]-3-[3-(4-cyanophenoxy)phenyl]urea (5 μM, 24 hours) significantly increases the apoptosis of LX2 cells and down-regulate p-STAT3 only in cells which are over-expressed the wild-type SHP-1 but not in cells treated with dN1 and D61A mutant; column represents the mean, and the error bar represents the standard deviation; ***P<0.001, and n=3-5 for each group.

Figure 17F:
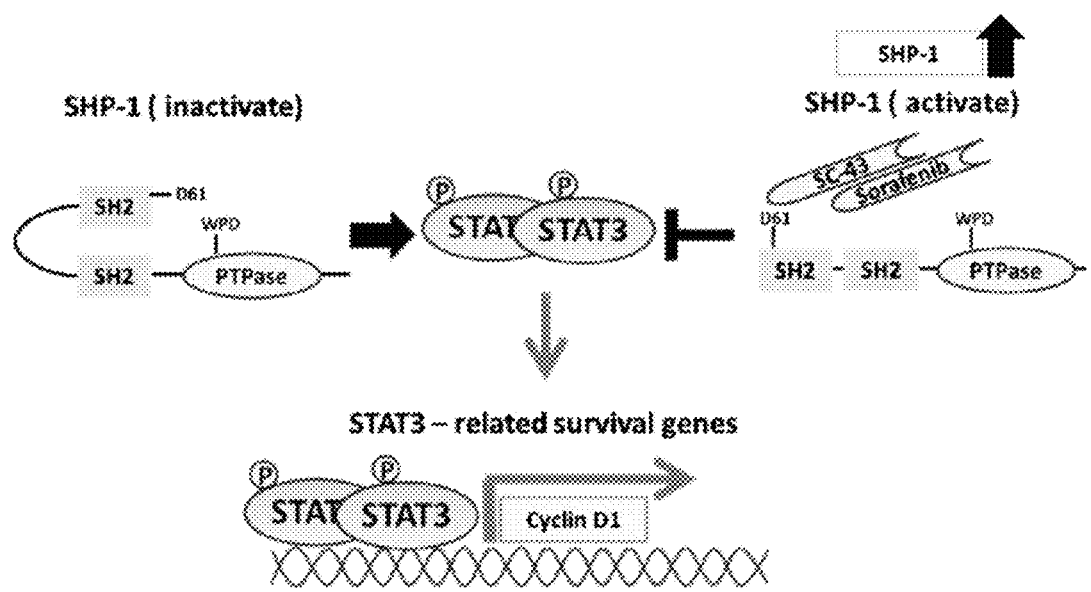

FIG. 17F shows the schematic diagram of the anti-fibrotic mechanism of 1-[4-chloro-3-(trifluoromethyl)phenyl]-3-[3-(4-cyanophenoxy)phenyl]urea through the SHP-1-STAT3 pathway.

DETAILED DESCRIPTION OF THE PREFERRED EMBODIMENT

All technical and scientific terms used herein have the same meaning as commonly understood by those having ordinary skill in the art, unless otherwise defined. All publications mentioned herein are hereby incorporated by reference in their entirety to disclose and describe methods and/or materials related to the cited publications.

As used herein, the singular forms "a", "an" and "the" including plural objects unless the context clearly dictates otherwise. Thus, for example, reference to "a sample" includes a plurality of such samples and equivalents known to those having ordinary skill in the art.

The "fibrosis" or "fibrotic disease" described herein is caused by various injury such as inflammation, infection, immune response, ischemia, chemical substances, radiation, etc. in the lungs, liver, kidney, blood vessels, peritoneum, pancreas, skin and other tissues and organs. After the injury, the fibroblasts begin to proliferate, the fibrous connective tissue in the tissues and organs increases, the parenchymal cells decrease, and the structures of tissues and organs are destroyed and the function are lost. The term fibrosis or "fibrotic disease" covers various causes of cardiac fibrosis, pulmonary fibrosis, hepatic fibrosis, renal fibrosis, vascular fibrosis, skin fibrosis (sclerosis) and other tissue and organ fibrotic lesions. The term fibrosis also includes cardiac fibrosis, pulmonary fibrosis, hepatic fibrosis, renal fibrosis, vascular fibrosis, skin fibrosis (sclerosis) and other tissue and organ fibrotic lesions, which are associated with the development or progression of various diseases.

The "hepatic fibrosis" describes herein is abnormal hyperplasia of connective tissue in the liver, excessive precipitation of diffuse extracellular matrix in the liver, pathological changes in the normal structure of the liver (lesion), which are caused by or accompanied by inflammation, infection (e.g. viral infection), immune response, ischemia, chemicals, radiation, oxidative stress and alcohol abuse, etc. Hepatic fibrosis further developing into cirrhosis is also covered by the term "hepatic fibrosis" in the present invention.

The "pulmonary fibrosis" describes herein is pathological processes caused by lung tissue mesenchymal cell proliferation, extracellular matrix hyperplasia and lung parenchyma remodeling, which result from or accompanied by inflammation, infection (e.g. viral infection), immune response, ischemia, chemicals, and radiation, etc.

The "treatment" describes herein includes the prevention of the particular disorder or condition, or the alleviation of symptoms associated with a particular disorder or condition and/or the prevention or elimination of the condition.

The "prevention" describes herein is the treatment to reduce or minimize the risk of a disease state in a patient who has not yet presented a clinical disease symptom, while the secondary prevention is defined as minimizing or reducing the recurrence, or the second occurrence of the same or similar clinical disease symptom.

The "individual" or "subject" describes herein is an animal, such as a human, but can also be a pet (e.g., a dog, a cat, and an analog), an economic animal (e.g., a cow, a sheep, a pig, a horse, and an analog) or an experimental animal (e.g., a rat, a mouse, a guinea pig, and an analog), the animal requires the treatment as described herein The "effective amount" describes herein is the amount of active agent required to achieve a therapeutic effect on an individual, whether used alone or in combination with one or more other active agents. Depending on the route of administration, the use of the excipients, and the use in conjunction with other active agents, the effective amounts will vary, as be recognized by those having ordinary skill in the art.

Suitable routes of administration includes, for example, oral, rectal, mucosal, or enteral administration, and parenteral delivery, which includes intramuscular, subcutaneous, intramedullary, and intrathecal, direct ventricular, intravenous, peritoneal, intranasal or intraocular injection, and can be a supplemental or sustained release dosage form.

The pharmaceutical compositions of the present invention can be made in a manner known in the art, for example, by conventional mixing, dissolving, emulsifying, embedding, encapsulating, or lyophilizing processes. Thus, the pharmaceutical compositions of the present invention can be formulated in a conventional manner using one or more physiologically acceptable carriers, including excipients and/or adjuvants, to aid in the processing of the active compounds to form pharmaceutically usable preparation. The "acceptable" describes herein means that the carrier must be compatible with the active ingredient of the composition (and preferably, the active ingredient is stable) and not deleterious to the individual being treated. The appropriate dosage form will depend on the route of administration chosen.

In particular, for administration by injection, the compounds of the present invention can be formulated in physiologically compatible buffers such as Hank buffer, Ringer's buffer or physiological saline buffer. For oral administration, the compounds of the present invention can be formulated by combining the active compound with pharmaceutically acceptable carriers known in the art, such as lactose, sucrose, mannitol, sorbitol, corn starch, wheat starch, rice starch, potato starch, gelatin, tragacanth, methylcellulose, hydroxypropylmethylcellulose, sodium carboxymethylcellulose, and/or polyvinylpyrrolidone (PVP, polyvinylpyrrolidone) to make the compound of the present invention be formulated into a tablet, a pill, a dragee, a capsule, a liquid, a gel, a syrup, a slurry, a suspension and the analog. For administration by inhalation, the compound of the present invention can be formulated as an aerosol spray sprayed from a pressurized container or sprayer, in combination with a suitable propellant, for example, dichlorodifluoromethane, trichlorofluoromethane, dichlorotetrafluoroethane, carbon dioxide or other suitable gas.

Example 1

Preparation of the Compound 1-[4-chloro-3-(trifluoromethyl)phenyl]-3-[3-(4-cyanophenoxy)phenyl] urea 4-Chloro-3-(trifluoromethyl)aniline (0.21 g, 1.1 mmol) and triethylamine (2 equiv) were added to 50 mL of a THF solution containing triphosgene (0.30 g, 1.0 mmol). The mixture was heated to 50° C. and heated for 30 minutes. After the temperature was lowered to room temperature, 4-(4-aminophenoxy)benzonitrile dissolved in 10 mL of a THF solution was added to the mixture, and heated again to 50° C. for 30 minutes. The mixture was evaporated, and then was diluted with water and extracted with ethyl acetate (EtOAc). The extract was washed with brine, dried over by anhydrous magnesium sulfate and the concentrates under reduced pressure to get 1-(3-(4-cyanophenoxy)phenyl)-3-(4-chloro-3-(trifluoromethyl)phenyl)urea) (0.34 g, 80%), and the compound is named SC-43 in the present invention.

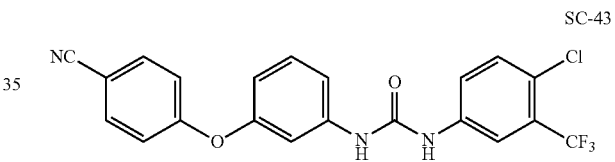

SC-43

Proton nuclear magnetic resonance ($^1$H-NMR) spectra were recorded on a nuclear magnetic resonance spectrometer (Bruker DPX300 (400 MHz)). The chemical shift system was reported as a δ value (ppm) low magnetic field from deuterated chloroform inside the indicated organic solution. The multiplicity of peaks was expressed as follows: s, singlet; d, doublet; t, triplet; q, quartet; dd, doublet of doublets; ddd, doublet of doublet of doublets; dt, Doublet of triplets; brs, broad single; m, multiplet. The coupling constant (J value) was expressed in Hertz (Hz). The progress of the reaction was determined by thin layer chromatography analysis (TLC) on a silica gel 60 F254 plate (Merck). Purification of the chromatographic analysis was carried out on a silica gel column 60 (0.063-0.200 mm or 0.040-0.063 mm, Merck) in an alkaline silicone. Commercially available reagents and solvents were used without further purification. The chemical formulas were as follows: CDCl$_3$, deuterated chloroform; DMSO-d6, dimethyl hydrazine-d6; EtOAc, ethyl acetate; DMF, N,N-dimethylformamide; MeOH, methanol; THF, tetrahydrofuran; EtOH, ethanol; DMSO, dimethyl hydrazine; NMP, N-methylpyrrolidone. High resolution mass spectra were recorded on a FINNIGAN MAT 95S mass spectrometer.

$^1$H NMR (400 MHz, DMSO): δ 9.17 (s, 1H), 9.03 (s, 1H), 8.04 (d, J=2.4 Hz, 1H), 7.83 (d, J=8.8 Hz, 2H), 7.64-7.55 (m, 2H), 7.41-7.32 (m, 2H), 7.23 (d, J=7.2 Hz, 1H), 7.11 (d, J=8.0 Hz, 2H), 6.75 (dd, J=8.0 Hz, 2.4 Hz, 1H); Calculated for C$_{21}$H$_{12}$N$_3$O$_2$F$_3$Cl [M-H]$^-$: 430.0570. Found: 430.0576.

Example 2

Bioassay

The present invention related to the pathway of SRC homology region 2-containing tyrosine phosphatase-1 (SHP-1)-signal transducer and activator of transcription 3 (STAT3) in fibrosis, and the evaluation of anti-fibrotic efficacy resulting from both in vitro and in vivo 1-[4-chloro-3-(trifluoromethyl)-phenyl]-3-[3-(4-cyanophenoxy)phenyl] urea. The present invention enhanced the activity of SHP-1 in fibrotic lung and liver. The experimental pulmonary fibrosis mouse model was set up by intranasal instillation of bleomycin in male C57BL/6J mice; and the experimental hepatic fibrosis mouse model was set up by injection of carbon tetrachloride ($CCl_4$), and bile duct ligation (BDL) in male C57BL/6J mice, and these two models were used to test 1-[4-chloro-3-(trifluoromethyl)-phenyl]-3-[3-(4-cyanophenoxy)phenyl]urea. Human lung epithelial cells (A549 cell line), mouse fibroblasts (NIH3T3 cell line), and rat, human, and mouse hepatic stellate cells (HSC) were used for in vitro cell research, especially with a focus on SHP-1/STAT3 signaling pathway.

2.1 Materials and Methods

Sorafenib (Nexavar® film-coated tablets) was supplied by Bayer HealthCare AG (Berlin, Germany) Smooth muscle actin ($\alpha$-SMA), phosphorylated STAT3 (Tyr705), STAT3, cyclin D1, glyceraldehyde-3-phosphate dehydrogenase, P-Smad2 (Ser465/467), P-Smad3 (Ser423/425), Smad2, Smad3, poly(ADP-ribose) polymerase (PARP), platelet-derived growth factor receptor $\beta$ (PDGFR-$\beta$), P-PDGFR-$\beta$ (Tyr857) and P-Akt (Ser473) were purchased from Cell Signaling (Massachusetts, USA). Akt was purchased from Santa Cruz Biotechnology (California, USA). Sodium vanadate was purchased from Cayman Chemical (Michigan, USA). PTP inhibitor III was purchased from Calbiochem (California, USA). Polyoxyethylene castor oil (Cremophor) was obtained from Sigma (Missouri, USA).

2.2 Experimental Procedure

2.2.1 Animal Model

Male C57BL/6J mice (6-8 weeks of age) were obtained from the National Laboratory Animal Center (Taipei, Taiwan). All experimental procedures using these mice were performed according to protocols approved by the Institutional Laboratory Animal Care and Use Committee of Cardinal Tien Hospital. Each mouse was housed in cages (IVC; individual ventilation cage), and given daily photoperiod for 12 hours. Room temperature was maintained at 22-25° C., and humidity was maintained at 60 to 70%. Ventilation rate was remained at 16-18 times/hour. Food and drinking water (Altromin 1326 mice feed, Altromin, Germany) was freely given. All operations were executed in accordance with the standards of animal experimental animal operation of law. Management and feeding of animals were in compliant with guidance for care and use of laboratory (NRC 1996) rule approach implementation.

2.2.2 Bleomycin-Induced Pulmonary Fibrosis

Figure 1:
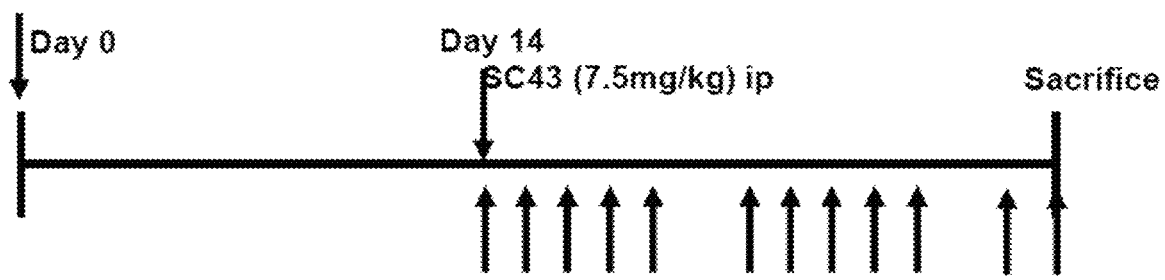
FIG. 1 shows the schematic diagram of an experimental
acute lung injury model of the bleomycin-induced pulmonary fibrosis in mice.

Pulmonary fibrosis was induced using bleomycin sulfate in male C57BL/6J mice (FIG. 1). The mice were intraperitoneally injected (IP) under anesthesia with Avertin (240 mg/Kg). On day 0 (n=20), a single dose of bleomycin (BLM) (1 mg=1000 IU, clinical level, Bleomycine Bellon, Sanofi-Aventis, France) was received in the mice (3.5 mg/kg) via intranasal instillation. The mice in the control group (n=10) were given saline only. On day 14 after intranasal BLM instillation, BLM treated mice were randomized into two groups receiving vehicle or 1-[4-chloro-3-(trifluoromethyl)phenyl]-3-[3-(4-cyanophenoxy)phenyl] urea until the end of the experiment. From day 14 to day 28, mice were administered intraperitoneally with 7.5 mg/kg/day of 1-[4-chloro-3-(trifluoromethyl)phenyl]-3-[3-(4-cyanophenoxy)phenyl]urea daily at a dose of 10 mL/kg body weight. The experimental time was 28 days and the 1-[4-chloro-3-(trifluoromethyl)phenyl]-3-[3-(4-cyanophenoxy)phenyl]urea compound was administered within 14 to 28 days.

2.2.3 Immunohistochemical Staining

The paraffin embedded tissue array blocks were cut into 4-μm-thick sections for H&E staining. For each case, carcinoma type, cell differentiation, growth pattern, tumor cell nuclear morphology, metaplasia, calcification, necrosis, mitosis count, invasion status and other specific differentiations were re-checked by two pathologists Immunohistochemical (IHC) staining was performed using a Ventana BenchMark XT automated stainer (Ventana, Tucson, Ariz.). Briefly, 4-μm-thick sections were cut consecutively from formalin-fixed, paraffin-embedded tissue. These sections were then mounted on silanized slides and allowed to dry overnight at 37° C. After deparaffinization and rehydration, the slides were incubated with 3% hydrogen peroxide solution for 5 minutes. After being washed with the supplied buffer, the tissue sections were repaired for 40 minutes with ethylenediamine tetraacetic acid.

2.2.4 Cell Culture

Murine NIH3T3 fibroblasts and human lung epithelial cells (A549 cells) were purchased from the Bioresource Collection and Research Center (Hsinchu, Taiwan). Cells were cultured in Dulbecco's modified eagle medium (DMEM) containing 10% fetal bovine serum (FBS), 100 μg/mL penicillin, 100 μg/mL streptomycin. Cells were cultured at 37° C. in a humidified atmosphere of 5% $CO_2$ and passaged every 4 to 5 days at 1:4 ratios.

Rat immortal hepatic stellate cell line HSC-T6 and LX2 human hepatic stellate cell line were provided by Professor Scott Friedman of Mount Sinai Hospital in New York, USA. The primary mouse HSCs were obtained via the way: after intubating the hepatic portal vein of the mouse, the cells were perfused with Leffert's and ethylene glycol bis-aminoethyl ether tetraacetic acid (EGTA) buffer in situ, and then collagenase was injected to digest the liver tissue, and then the primary mouse HSCs were isolated by Histodnz gradient. HSC-T6 cells were cultured in Waymouth medium; LX2 cells and primary mouse HSCs were cultured in Dulbecco's Modified Eagle Medium (DMEM) containing 10% fetal bovine serum (FBS), 100 μg/mL penicillin, 100 μg/mL streptomycin, and 2 mM L-glutamine HSC-T6 cells, LX2 cells and primary mouse HSCs were cultured in a humidified incubator containing 5% carbon dioxide at 37° C. After adding the FBS, the resting HSC is started. For in vitro studies, various concentrations of 1-[4-chloro-3-(trifluoromethyl)phenyl]-3-[3-(4-cyanophenoxy)phenyl]urea and sorafenib were dissolved in dimethyl sulfoxide and subsequently added to cells, which were in 5% FBS, for a predetermined period of time.

2.2.5 Hydroxyproline Analysis

Hydroxyproline analysis was performed using a hydroxyproline test kit following the manufacturer's instructions (Cell BioLabs, Inc., USA). Lung tissue was hydrolyzed in 12N HCl at 120° C. for 3 hours, and then washed and suspended in $H_2O$. The tissue suspension was then mixed with chloramine-T at room temperature for 30 minutes. Then Ehrlich's reagent was added and reacted at 60° C. for 90 minutes. After that, the absorbance at 540 nm was measured.

2.2.6 Collagen Content Analysis

Mice lung collagen was measured in lung homogenate using a Sircol assay (Biocolor, UK) following the manufacturer's instructions. Briefly, lung tissue homogenates were mixed with Sircol dye and centrifuged. The precipitate was resuspended in NaOH and the absorbance at 550 nm was measured. The absorbance obtained is directly proportional to the concentration of the recently synthesized collagen.

2.2.7 Western Blot Analysis

Whole-cell extracts were obtained via RIPA buffer (Millipore, USA) and protein concentrations were quantified via a BCA protein assay kit (Thermo Fisher Scientific, USA). 20 or 25 µg of protein was added to various percentages of SDS-sodium dodecyl sulfate-acrylamide gel and blotted onto a polyvinylidene fluoride (PVDF) membrane. The membrane was then reacted with a primary antibody; after extensive washing, the membrane was reacted with a horseradish peroxidase (HRP) blocking buffer containing a second antibody. Proteins were detected by Immobilon Western Chemiluminescent HRP substrate (Millipore, USA) or ECL detection system (UVP Corporation, USA).

2.2.8 Antibodies

Antibodies for immunoblotting techniques such as anti-E-cadherin, anti-Fibronectin, anti-N-cadherin were purchased from Abcam (UK). Other antibodies such as anti-SHP-1, anti-phosphorylated STAT3(Tyr705), anti-STAT3α-smooth muscle actin (α-SMA) and anti-caspase-9 were purchased from Cell Signaling Corporation (Malaysia, United States).

2.2.9 Cell Viability Assay

Murine NIH3T3 fibroblasts were seeded into 96-well plates ($1 \times 10^3$ cells/well). To measure the cell viability and the cell proliferation, 10% WST-1 (cell proliferation reagent WST-1, Roche) was added to each well and reacted for 3 hours. The reaction was catalyzed by mitochondrial reductase in active cells and the optical density (OD) was calculated by measuring the absorbance at 450 nm via a Bio-Rad ELISA analyzer.

HSC-T6 cells, LX2 cells or primary mouse HSCs cells were seeded in 96-well plates (5,000 cells/well) for 24 hours, and the cells were treated with various concentrations of 1-[4-chloro-3-(trifluoromethyl)phenyl]-3-[3-(4-cyanophenoxy)phenyl]urea or Sorafenib for 24 or 48 hours. The effect of each reagent on the cell viability and the cell were evaluated by CellTiter 96 AQueous one solution of 3-(4,5-dimethylthiazol-2-yl)-5-(3-carboxymethoxyphenyl)-2-(4-sulfophenyl)-2H-tetra zolium, an inner, MTS (Promega, USA). The experiment was carried out following the manufacturer's instructions, and each group was triple repetition. After 24 hours of treatment with 1-[4-chloro-3-(trifluoromethyl)phenyl]-3-[3-(4-cyanophenoxy)-phenyl]urea or sorafenib, the cells were double stained with Annexin V and propidium iodide. The proportion of apoptotic cells was mixed the early (Annexin V+/PI−) and the late (Annexin V+/PI+) apoptotic cells measured by BD FACS Verse flow cytometry (BD, USA).

2.2.10 Apoptosis Analysis

The measurement of apoptotic cells was conducted by flow cytometry (sub-G1) and cell death detection enzyme-bound immunosorbent assay (ELISA) for cytoplasmic histone associated DNA fragments. The amount of formazan dye was quantified by measuring the absorbance at 570 nm using ELISA reader to calculate the optical density (OD) values. Statistical analysis was determined using Student's t-test, with $P<0.05$ considered significant.

2.2.11 Ectopic Expression of STAT3

STAT3 cDNA (KIAA1524) was purchased from Addgene Platinum Corporation. After the transient transfection of STAT3, SHP-1, SHP-1(dN1) mutants and SHP-1(61A) mutant in mouse fibroblasts (NIH3T3 cell line) and human lung epithelial cells (A549 cell line), cells were reacted separately with the 1-[4-chloro-3-(trifluoromethyl)phenyl]-3-[3-(4-cyanophenoxy)phenyl]urea compound and subjected to the Western blotting process. Transfection was performed by X-tremeGENE HP Transfection Reagent (Roche, Germany) following the manufacturer's instructions.

2.2.12 SHP-1 Phosphatase Activity

After drug treatment, mouse fibroblasts (NIH3T3 cell line), human lung epithelial cells (A549 cell line) or LX2 cell protein extract were reacted with anti-SHP-1 antibody in immunoprecipitation buffer overnight. Protein A/G Sepharose Fast Flow Beads (GE) were added to each sample, followed by a rotation reaction at 4° C. for 3 hours. The 96EnzChek® tyrosine phosphatase assay kit (R-22067) was used for SHP-1 activity assay (Invitrogen, USA).

2.2.13 Gene Knockout by siRNA

Smart-pool siRNA, including control (sc-37007) siRNA, siRNA anti-SHP-1, and STAT3, were purchased from Santa Cruz Biotechnology (California, USA).

2.2.14 SHP-1 Expression in Patients with Liver Fibrosis

Twenty-five patients with chronic hepatitis B, who had various degrees of liver fibrosis, were recruited (F0, F1, F2, F3, and F4, respectively, n=5 for each group). Their biopsy liver tissue was stained with SHP-1 or α-SMA. The study was in line with the ethical code of the Declaration of Helsinki in 1975 and was approved by the Ethics Committee of the Taiwan University Hospital. All patients received written informed consent at the time of admission.

2.2.15 Hepatic Fibrosis Mouse Model

In male C57BL/6J mice, liver fibrosis was induced by carbon tetrachloride ($CCl_4$). The mice were given peritoneal injection of carbon tetrachloride for 4 or 8 weeks every two weeks. The mice were given a polyoxyethylene castophor carrier, 1-[4-chloro-3-(trifluoromethyl)phenyl]-3-[3-(4-cyanophenoxy)phenyl]urea (5, 10, or 20 mg/kg, respectively) or sorafenib (sorafenib) every five days per week during the specified period until they were sacrificed; sorafenibine has been shown to have anti-fibrotic activity, so it is used as a positive control group.

In the bile duct ligation (BDL) mouse model, the common bile duct of Balb/C mice was double-ligated and excised. Mice were fed daily with vehicle or 1-[4-chloro-3-(trifluoromethyl)phenyl]-3-[3-(4-cyanophenoxy)phenyl]urea on day 1 or day 8 until they were sacrificed on day 14.

2.2.16 Histological Analysis of Hepatic Fibrosis

The mice liver samples were stored in 10% formaldehyde, dehydrated with gradient alcohol, embedded in paraffin blocks, sectioned to a thickness of 3 µm, placed on glass slides, and stained with Picrosirius Red Stain kit (ScyTek, USA), following the manufacturer's instructions. The severity of liver fibrosis was graded according to the Ishak fibrosis score. Quantitative collagen-positive area (qCPA) was determined by densitometry via ImageJ software. Hepatic hydroxyproline concentrations were measured by the hydroxyproline assay kit (Biovision, USA), following the manufacturer's instructions Immunohistochemistry was performed by the Leica BOND-MAX automatic chromatograph (Leica Biosystems, Germany), following the manufacturer's instructions.

2.2.17 Transforming Growth Factor-β Induction

For transforming growth factor (TGF)-β induction, the HSCs were serum deprived for 4 hours, subsequently treated with 10 µM 1-[4-chloro-3-(trifluoromethyl)phenyl]-3-[3-(4-cyanophenoxy)phenyl]urea for 4 hours, and followed by stimulation with 10 ng/mL recombinant human TGF-β1 (R&D Systems, Minneapolis, Minn., USA) for 20 minutes.

2.2.18 Platelet-Derived Growth Factor-BB Induction

For platelet-derived growth factor (PDGF)-BB induction, LX2 cells or HSC-T6 cells were serum deprived for 4 hours, treated with 10 µM 1-[4-chloro-3-(trifluoromethyl)phenyl]-3-[3-(4-cyanophenoxy)phenyl]urea for 4 hours, followed by induction with 100 ng/mL recombinant human or rat PDGF-BB (R&D Systems, USA) for 10 minutes.

2.2.19 Interleukin-6 Stimulation

For interleukin (IL)-6 stimulation, the HSCs were serum deprived for 4 hours, treated with 10 µM 1-[4-chloro-3-(trifluoromethyl)phenyl]-3-[3-(4-cyanophenoxy)phenyl] urea for 4 hours, followed by induction with 100 ng/mL IL-6 (R&D Systems, USA) for 30 minutes.

2.2.20 Plasmid, siRNA, and Transfection

Rat STAT3 (Open Biosystem, Pittsburgh Pa., USA) was constructed into a pLVX-AcGFP-N1 expression vector (Clontech, Mountain View, Calif., USA), which was later co-transfected into 293FT cells in addition to lentiviral packaging and expression vectors (P8.91 and VSV-G) by using the Lipofectamine 2000 transfection reagent (Invitrogen, USA). The lentiviral supernatant was harvested 48 hours post transfection and used to infect $5 \times 10^5$ HSC-T6 cells, which were seeded on a 6-cm dish; the rat STAT3 stable overexpression clone was generated.

Plasmids encoding the human wild-type SHP-1 and SHP-1 mutant, in which the N—$SH_2$ domain was truncated (dN1) or one aspartic acid at site 61 was changed into an alanine residue (D61A) were cloned into the pCMV6-entry vector with myc-tag. These mutants were confirmed through DNA sequencing. Smart-pool siRNA, including the control (D-001810-10), and SHP-1 (PTPN6, L-009778-00-0005) were obtained from Dharmacon Inc. (Chicago, Ill., USA). For transient expression, SHP-1 plasmids or siRNA (final concentration, 100 nM) with the Lipofectamine 2000 transfection reagent were pretransfected into the LX2 cells for 24 h, following the manufacturer's instructions.

2.2.21 Colony Formation Assay

LX2 cells were plated in 10-cm dishes (1500-5000 cells per dish) and cultured in DMEM for 2 weeks. The cells were subsequently fixed with 4% formaldehyde and stained with 0.1% crystal violet.

2.2.22 Statistical Analysis

Continuous variables are presented as mean (standard error), and categorical data are presented as number (percentage), as appropriate. Differences between subgroups were evaluated using the Student t test. Spearman's correlation was used for the association between SHP-1 and serum alanine aminotransferase (ALT). The mouse survival rate was estimated using the Kaplan-Meier method. The log-rank test was used to determine the statistical differences in survival of the different experimental groups. Statistical analysis was performed using STATA (version 13, Stata Corp, College Station, Tex., USA). All tests were two-sided, and $P < 0.05$ was considered significant.

Example 3

1-[4-chloro-3-(trifluoromethyl)phenyl]-3-[3-(4-cyanophenoxy)phenyl]urea Treatment Reduces Pulmonary Fibrosis in Mice SRC homology region 2-containing tyrosine phosphatase-1 (SHP-1) is a regulator of different intracellular signaling molecules, such as signal transducer and activator of transcription 3 (STAT3), KIT, CD22, CD5, CD72, SHPS-1, TIMP (metallopeptidase inhibitor), CDK2, p27, SRC, ZAP70, interleukin-10 (IL-10), NF-κB, Lck, 3BP2, Lyn, and cyclin D1. STAT3 is a transcription factor that regulates cell growth and survival by modulating the expression of target genes. SHP-1 is a key regulator of STAT3 activity.

The present invention demonstrates the anti-pulmonary fibrosis activity of 1-[4-chloro-3-(trifluoromethyl)phenyl]-3-[3-(4-cyanophenoxy)phenyl]urea, indicating that the 1-[4-chloro-3-(trifluoromethyl)phenyl]-3-[3-(4-cyanophenoxy) phenyl]urea compound initiates the activity of SHP-1, down-regulates STAT3, and then reduces the survival rate of fibroblasts and epithelial transformation of epithelial mesenchymal transition (EMT).

The in vivo experimental data of the present invention also confirmed that 1-[4-chloro-3-(trifluoromethyl)phenyl]-3-[3-(4-cyanophenoxy)phenyl]urea improves pulmonary fibrosis induced by bleomycin in mice, indicating that 1-[4-chloro-3-(trifluoromethyl)phenyl]-3-[3-(4-cyanophenoxy)

phenyl]urea can be used for the treatment of idiopathic pulmonary fibrosis (IPF) and other fibrotic diseases.

Figure 2:
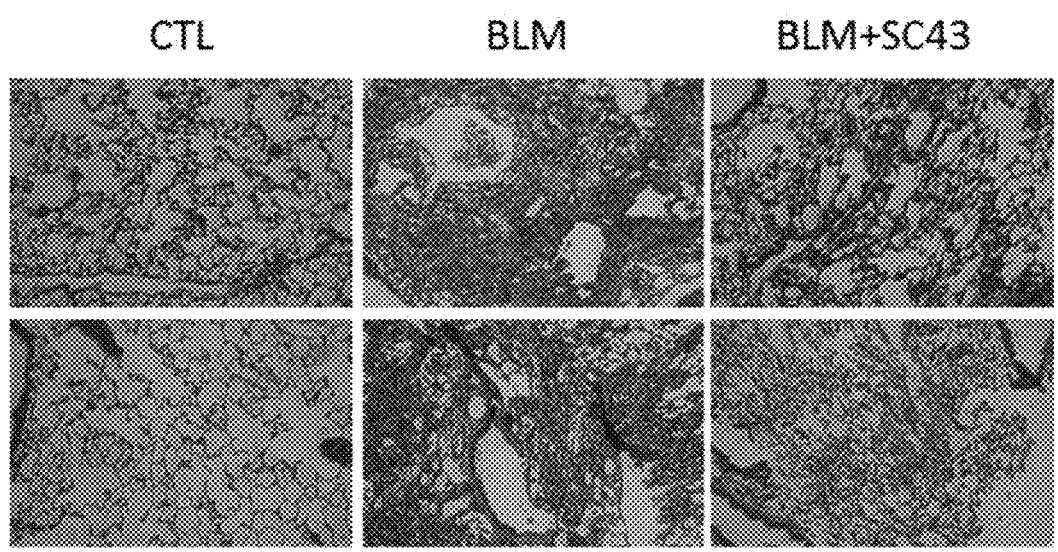
FIG. 2 shows the hematoxylin-eosin (H&E) staining
tissue diagram of improving the bleomycin-induced pulmonary fibrosis in mice by treating with 1-[4-chloro-3-(trifluoromethyl)phenyl]-3-[3-(4-cyanophenoxy)phenyl]urea. CTL
represents the control group; BLM represents the group of
the bleomycin-induced mice; BLM+SC43 represents the
group of the bleomycin-induced mice treated with 1-[4-chloro-3-(trifluoromethyl)phenyl]-3-[3-(4-cyanophenoxy)
phenyl]urea.
Figure 3:
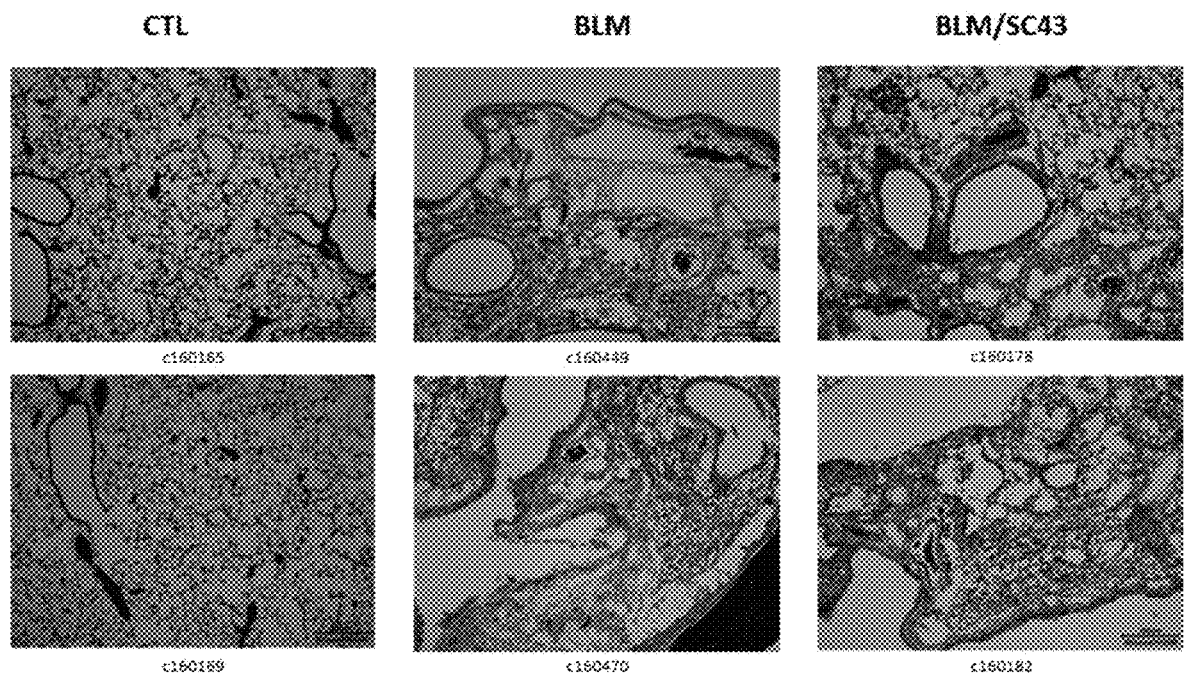
FIG. 3 shows the Masson's trichrome staining tissue
diagram of improving the bleomycin-induced pulmonary
fibrosis in mice by treating with 1-[4-chloro-3-(trifluoromethyl)phenyl]-3-[3-(4-cyanophenoxy)phenyl]urea. CTL represents the control group; BLM represents the group of the
bleomycin-induced mice; BLM+SC43 represents the group
of the bleomycin-induced mice treated with 1-[4-chloro-3-
(trifluoromethyl)phenyl]-3-[3-(4-cyanophenoxy)phenyl]
urea.

3.1 1-[4-chloro-3-(trifluoromethyl)phenyl]-3-[3-(4-cyanophenoxy)phenyl]urea Improves Pulmonary Fibrosis Induced by Bleomycin in Mice The present invention established an experimental acute lung injury model of bleomycin-induced pulmonary fibrosis (FIG. 1). The animal model, which was treated with a 7.5 mg/kg dose of 1-[4-chloro-3-(trifluoromethyl)phenyl]-3-[3-(4-cyanophenoxy)phenyl]urea via daily gavage, was well tolerated because no drug-related adverse events were observed. According to hematoxylin-eosin staining (H&E Stain) of lung sections, intranasal injection of BLM resulted in destruction of normal lung structure, significant proliferation of fibroblasts, infiltration of inflammatory cells, and massive deposition of fibrous collagen (FIG. 2, middle). More importantly, these pathological changes were significantly improved after administration of 1-[4-chloro-3-(trifluoromethyl)phenyl]-3-[3-(4-cyanophenoxy)phenyl]urea (FIG. 2, right); similarly, fibrin deposition was significantly reduced after administration of 1-[4-chloro-3-(trifluoromethyl)phenyl]-3-[3-(4-cyanophenoxy)phenyl]urea, as shown in Masson's trichrome staining positive area (FIG. 3).

Figure 4:
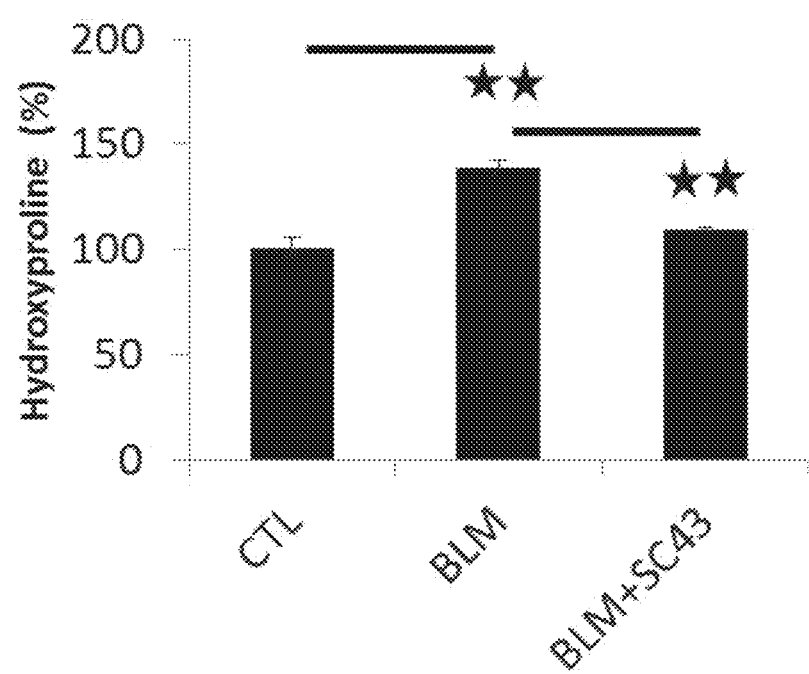
FIG. 4 shows the amount of hydroxyproline of improving
the bleomycin-induced pulmonary fibrosis in mice by treating with 1-[4-chloro-3-(trifluoromethyl)phenyl]-3-[3-(4-cyanophenoxy)phenyl]urea. CTL represents the control
group; BLM represents the group of the bleomycin-induced
mice; BLM+SC43 represents the group of the bleomycin-induced mice treated with 1-[4-chloro-3-(trifluoromethyl)
phenyl]-3-[3-(4-cyanophenoxy)phenyl]urea. The column
represents the mean; the error bar represents the standard
deviation; **p<0.05.
Figure 5:
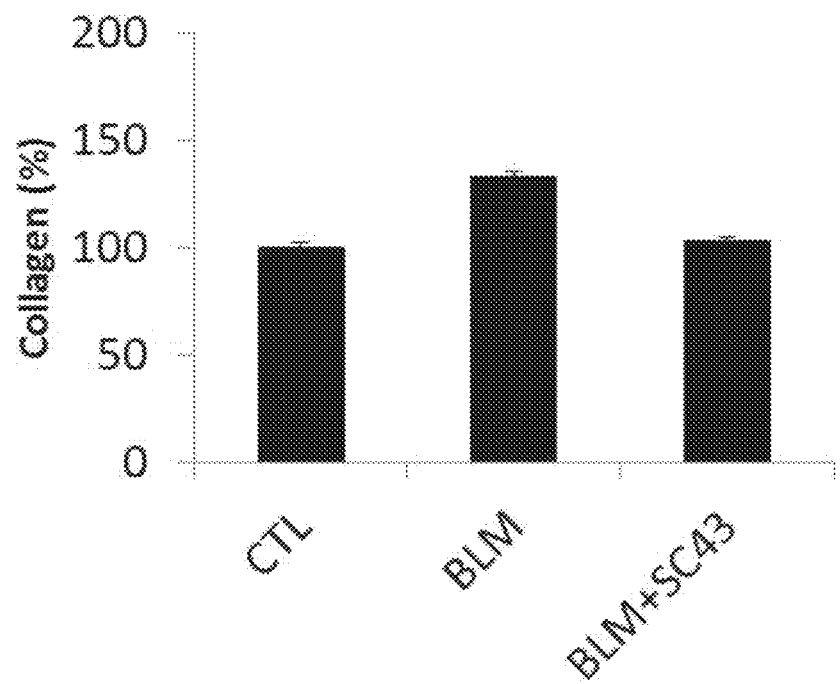
FIG. 5 shows the amount of collagen of improving the
bleomycin-induced pulmonary fibrosis in mice by treating
with 1-[4-chloro-3-(trifluoromethyl)phenyl]-3-[3-(4-cyanophenoxy)phenyl]urea. CTL represents the control group;
BLM represents the group of the bleomycin-induced mice;
BLM+SC43 represents the group of the bleomycin-induced
mice treated with 1-[4-chloro-3-(trifluoromethyl)phenyl]-3-
[3-(4-cyanophenoxy)phenyl]urea. The column represents
the mean; the error bar represents the standard deviation.
Figure 6:
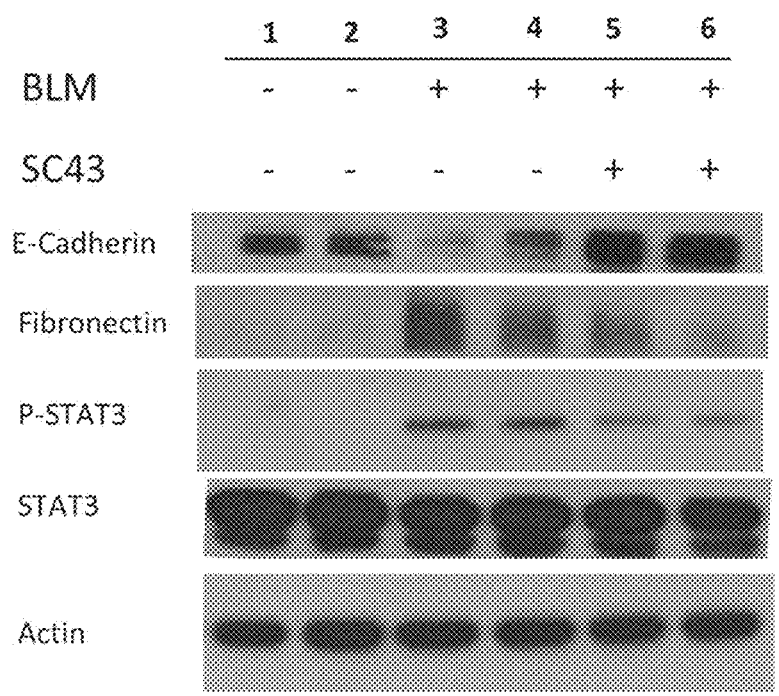
FIG. 6 shows the gel electropherogram of improving the
epithelial mesenchymal transition of the bleomycin-induced
pulmonary fibrosis in mice by treating with 1-[4-chloro-3-
(trifluoromethyl)phenyl]-3-[3-(4-cyanophenoxy)phenyl]-
urea.

Next, since hydroxyproline (Hyp) was a major component of collagen, the present invention detected the Hyp content of each group of mice to quantify the degree of the pulmonary fibrosis. As shown in FIG. 4, compared with the BLM group, the Hyp content decreased by about 22% after treatment of 1-[4-chloro-3-(trifluoromethyl)phenyl]-3-[3-(4-cyanophenoxy)phenyl]urea, indicating that 1-[4-chloro-3-(trifluoromethyl)phenyl]-3-[3-(4-cyanophenoxy)phenyl] urea had a protective effect on the accumulation of extracellular matrix (ECM). The present invention detected the collagen content of mice (FIG. 5) and showed that 1-[4-chloro-3-(trifluoromethyl)phenyl]-3-[3-(4-cyanophenoxy)phenyl]urea improved the accumulation of collagen in the pulmonary fibrosis model. The present invention further detected whether 1-[4-chloro-3-(trifluoromethyl)phenyl]-3-[3-(4-cyanophenoxy)phenyl]urea reduced epithelial mesenchymal transition (EMT), which was a key step in the occurrence of fibrosis; as shown in FIG. 6, compared with the control group (Line 1 and 2), the expression level of E-cadherin (epithelial phenotype protein) in bleomycin-induced pulmonary fibrosis mouse model reduced (Line 3 and 4). However, after treated with 1-[4-chloro-3-(trifluoromethyl)phenyl]-3-[3-(4-cyanophenoxy)phenyl]urea, the expression level of E-cadherin in bleomycin-induced pulmonary fibrosis mouse model increased (Line 5 and 6). Fibronectin was an interstitial phenotype marker that increased in the bleomycin-induced pulmonary fibrosis mouse model (Line 3 and 4), but after 1-[4-chloro-3-(trifluoromethyl)phenyl]-3-[3-(4-cyanophenoxy)phenyl]urea treatment (Line 5 and 6) the amount of fibronectin decreased. P-STAT3 increased in bleomycin-induced pulmonary fibrosis, but decreased after 1-[4-chloro-3-(trifluoromethyl)phenyl]-3-[3-(4-cyanophenoxy)phenyl]urea treatment.

Figure 7A:
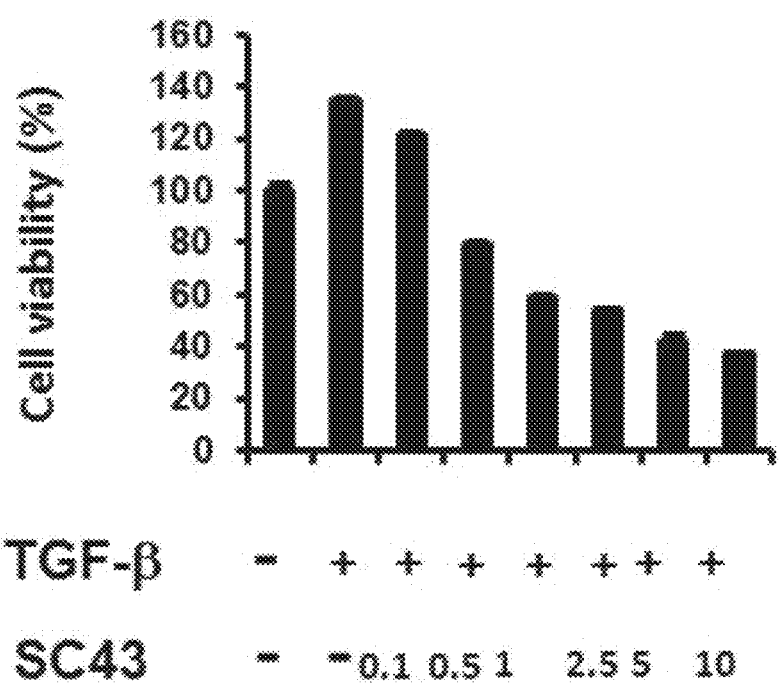
FIG. 7A shows the treatment of 1-[4-chloro-3-(trifluoromethyl)phenyl]-3-[3-(4-cyanophenoxy)phenyl]urea
reduces the survival rate of mouse fibroblasts (NIH3T3 cell
line) by the SHP-1/STAT3 signaling pathway.
Figure 7B:
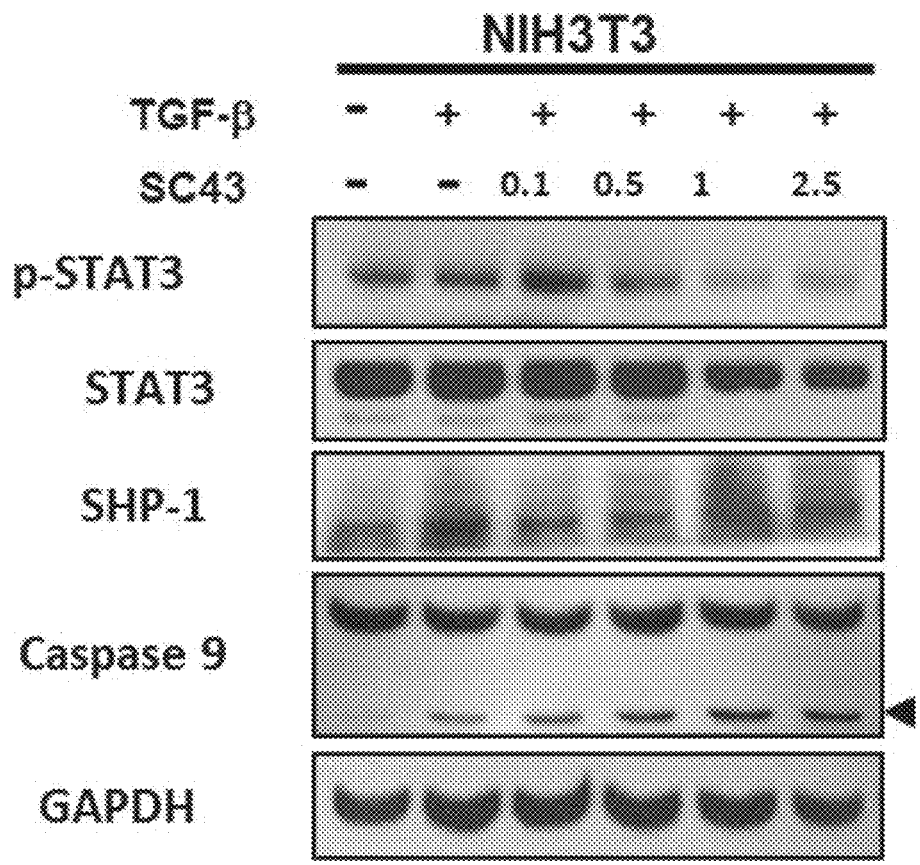
FIG. 7B shows the treatment of 1-[4-chloro-3-(trifluoromethyl)phenyl]-3-[3-(4-cyanophenoxy)phenyl]urea
reduces the expression level of p-STAT3 by the SHP-1/
STAT3 signaling pathway.
Figure 7C:
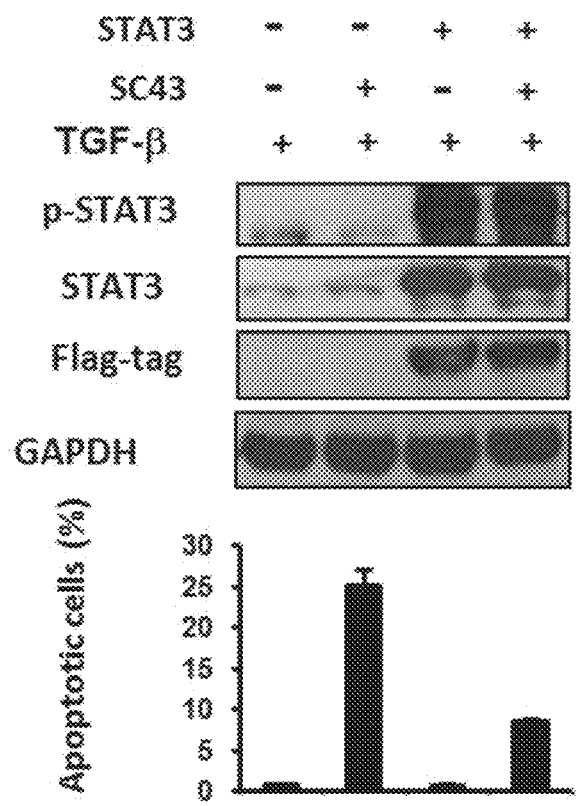
FIG. 7C shows the treatment of 1-[4-chloro-3-(trifluoromethyl)phenyl]-3-[3-(4-cyanophenoxy)phenyl]urea
induces the apoptosis by the SHP-1/STAT3 signaling pathway.
Figure 7D:
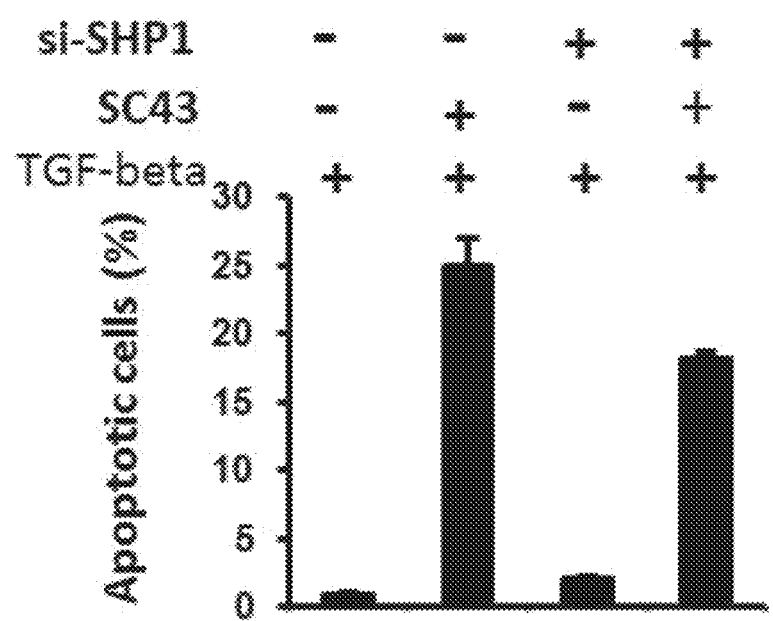
FIG. 7D shows the knockdown of SHP-1 offsets the cell
apoptosis caused by 1-[4-chloro-3-(trifluoromethyl)phenyl]-
3-[3-(4-cyanophenoxy)phenyl]urea in the SHP-1/STAT3
signaling pathway.

3.2 1-[4-chloro-3-(trifluoromethyl)phenyl]-3-[3-(4-cyanophenoxy)phenyl]urea Induces the Inhibition of STAT3 Via SHP-1 to Inhibit Cell Proliferation and Induce Apoptosis in Mouse Pulmonary Fibrosis The results of the above experiments prompted the present invention to further investigate the mechanism of the anti-fibrotic activity of 1-[4-chloro-3-(trifluoromethyl)phenyl]-3-[3-(4-cyanophenoxy)phenyl]urea. Treatment with 1-[4-chloro-3-(trifluoromethyl)phenyl]-3-[3-(4-cyanophenoxy)phenyl]urea reduced the survival rate of mouse fibroblasts (NIH3T3 cell line) in a dose-dependent manner (FIG. 7A); treatment with 1-[4-chloro-3-(trifluoromethyl)phenyl]-3-[3-(4-cyanophenoxy)phenyl]urea also reduced the expression level of p-STAT3 (FIG. 7B); 1-[4-chloro-3-(trifluoromethyl)phenyl]-3-[3-(4-cyanophenoxy)phenyl]urea rescued NIH3T3, which STAT3 overexpressed in, by inducing apoptosis (FIG. 7C); in addition, the apoptosis of 1-[4-chloro-3-(trifluoromethyl)phenyl]-3-[3-(4-cyanophenoxy)phenyl] urea was offset by SHP-1 knockout (FIG. 7D). These results indicated that 1-[4-chloro-3-(trifluoromethyl)phenyl]-3-[3-(4-cyanophenoxy)-phenyl]urea down-regulated p-STAT3 and induced apoptosis of fibrotic cells, whereas the inhibition of SHP-1 offset the effects of 1-[4-chloro-3-(trifluoromethyl)phenyl]-3-[3-(4-cyanophenoxy)phenyl]urea.

3.3 1-[4-chloro-3-(trifluoromethyl)phenyl]-3-[3-(4-cyanophenoxy)phenyl]urea Inhibits the TGF-β1-Induced the Formation of Epithelial Mesenchymal Transition (EMT) in Human Lung Epithelial Cells (A549 Cell Line)

Figure 8A:
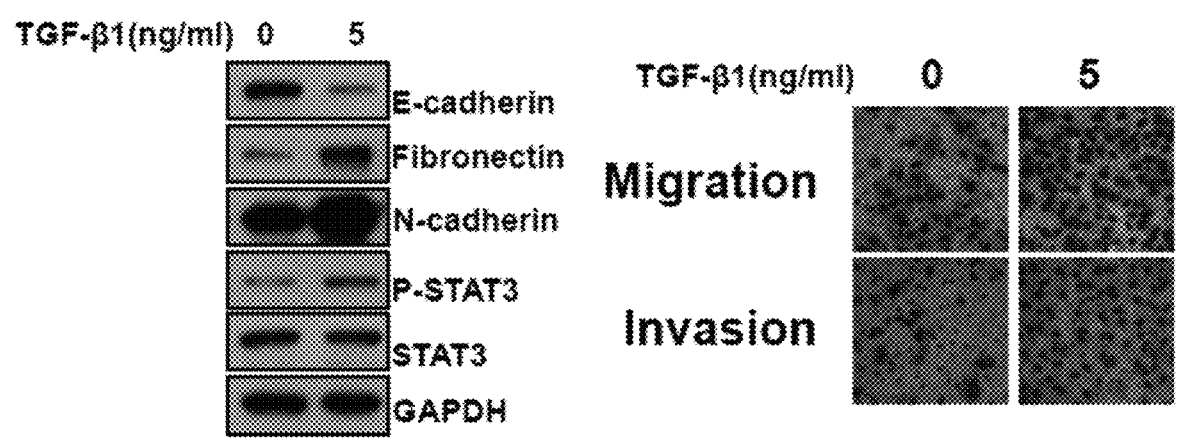
FIG. 8A shows the production of epithelial mesenchymal
transition (EMT) by exposing human lung epithelial cells
(A549 cell line) to TGF-β1. The expression of E-cadherin is
decreased; the expression of fibronectin and N-cadherin is
up-regulated; STAT3 phosphorylation is also increased after
exposure to TGF-β1 (left panel); invasion and migration of
EMT is increased after TGF-β1 stimulation (right panel).
Figure 8B:
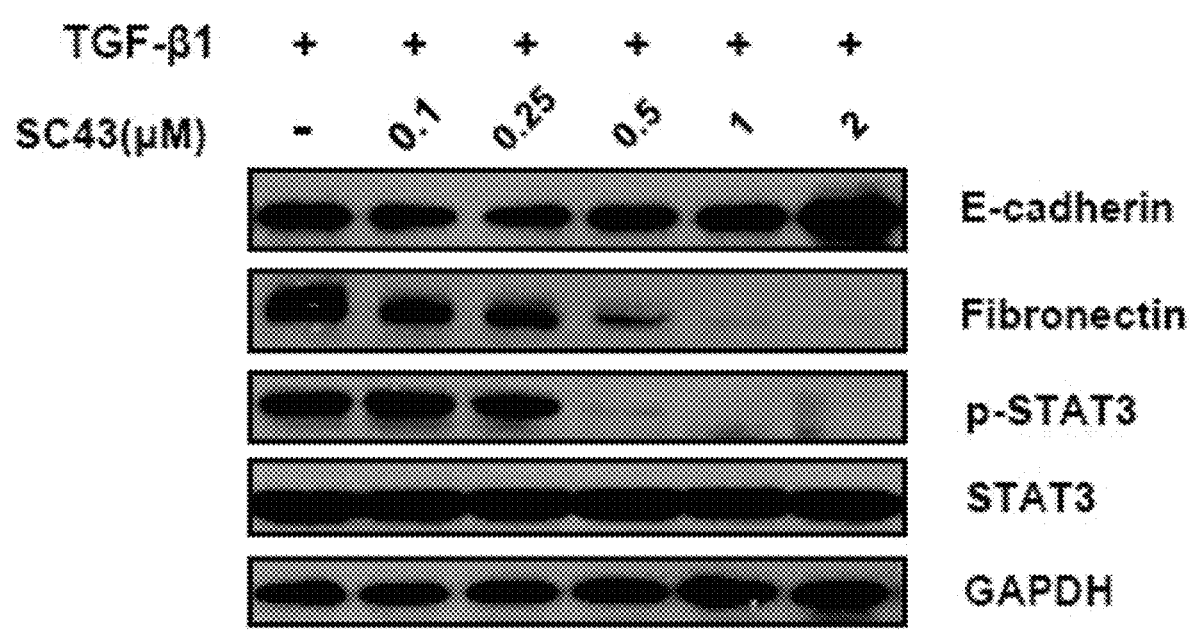
FIG. 8B shows the treatment of 1-[4-chloro-3-(trifluoromethyl)phenyl]-3-[3-(4-cyanophenoxy)phenyl]urea
inhibits the production of epithelial mesenchymal transition
(EMT) which is caused by exposing human lung epithelial
cells (A549 cell line) to TGF-β1. The expression of E-cadherin is increased; the expression of fibronectin and N-cadherin is decreased; STAT3 phosphorylation is also decreased
after exposure to TGF-β1.
Figure 8C:
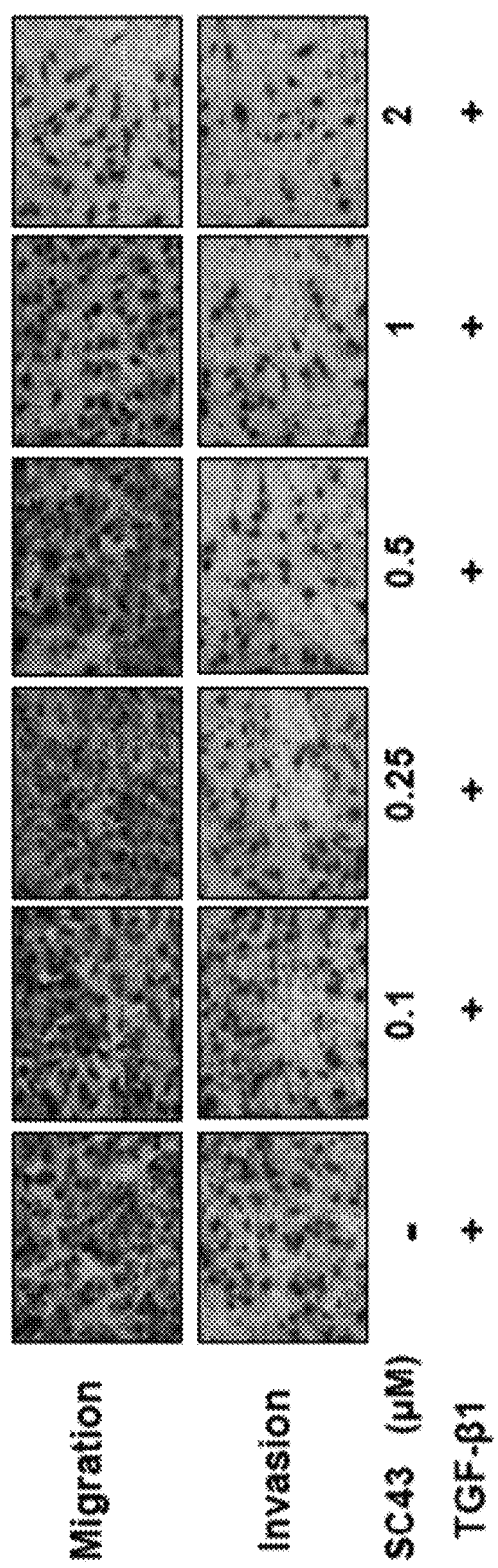
FIG. 8C shows the treatment of 1-[4-chloro-3-(trifluoromethyl)phenyl]-3-[3-(4-cyanophenoxy)phenyl]urea
inhibits the production of epithelial mesenchymal transition
(EMT) which is caused by exposing human lung epithelial
cells (A549 cell line) to TGF-β1. After treated with 1-[4-chloro-3-(trifluoromethyl)phenyl]-3-[3-(4-cyanophenoxy)
phenyl]urea, the EMT invasion and migration of cells
caused by TGF-β1 are decreased.
Figure 8D:
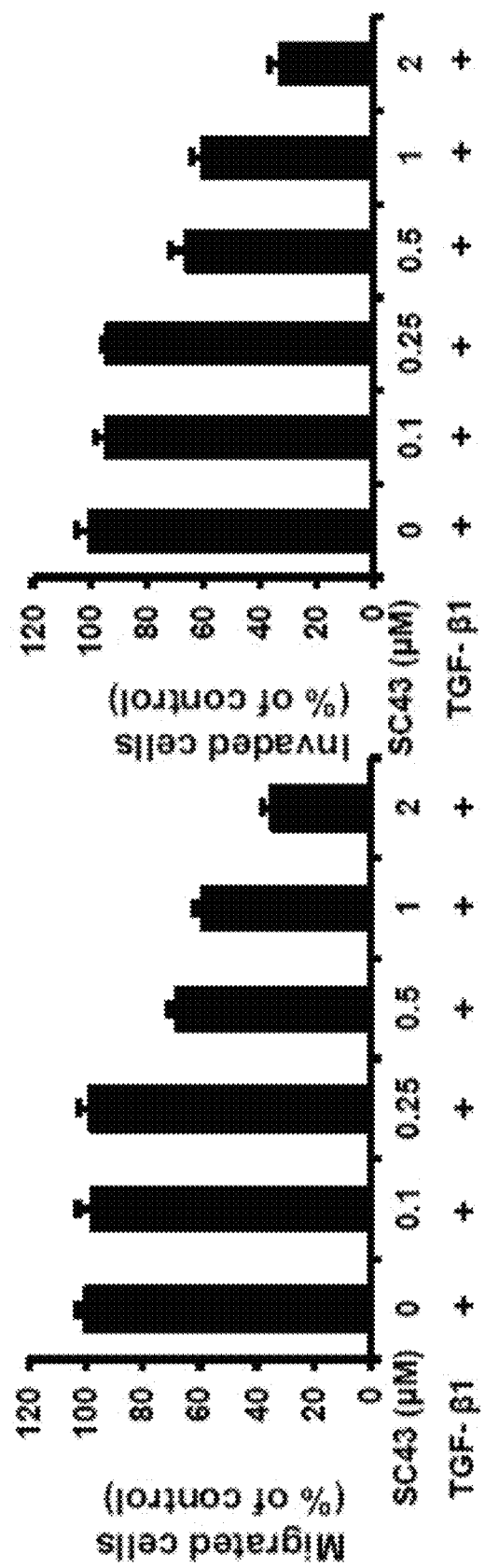
FIG. 8D shows the treatment of 1-[4-chloro-3-(trifluoromethyl)phenyl]-3-[3-(4-cyanophenoxy)phenyl]urea
inhibits the invasion and migration of epithelial mesenchymal transition (EMT) which is caused by exposing human
lung epithelial cells (A549 cell line) to TGF-β1.

In the process of pulmonary fibrosis, the activated fibroblasts were responsible for the production of epithelial mesenchymal transition (EMT) which was caused by the proliferation of alveolar extracellular matrices of alveolar epithelium cells and resident fibroblasts. The present invention utilizes A549 cells to evaluate the effect of 1-[4-chloro-3-(trifluoromethyl)phenyl]-3-[3-(4-cyanophenoxy)phenyl] urea on EMT. A549 cell was an alveolar type II epithelial cell line that has been widely used to study as an ideal in vitro model of EMT. A549 cells were exposed to TGF-β1 for 8 hours to be induced to EMT. The expression level of the adhesive junction protein E-cadherin decreased, and the expression level of the intermediate filament fibronectin and N-cadherin was up-regulated; in addition, STAT3 phosphorylation also increased after exposure to TGF-β1. (FIG. 8A, left). On the other hand, treatment of A549 cells with 1-[4-chloro-3-(trifluoromethyl)phenyl]-3-[3-(4-cyanophenoxy)phenyl]urea reversed TGF-β1-induced EMT in a dose-dependent manner, as shown by the EMT-tagged performance profile (FIG. 8B), and the migration and the invasion of cells were reduced (FIGS. 8C and 8D).

Figure 9A:
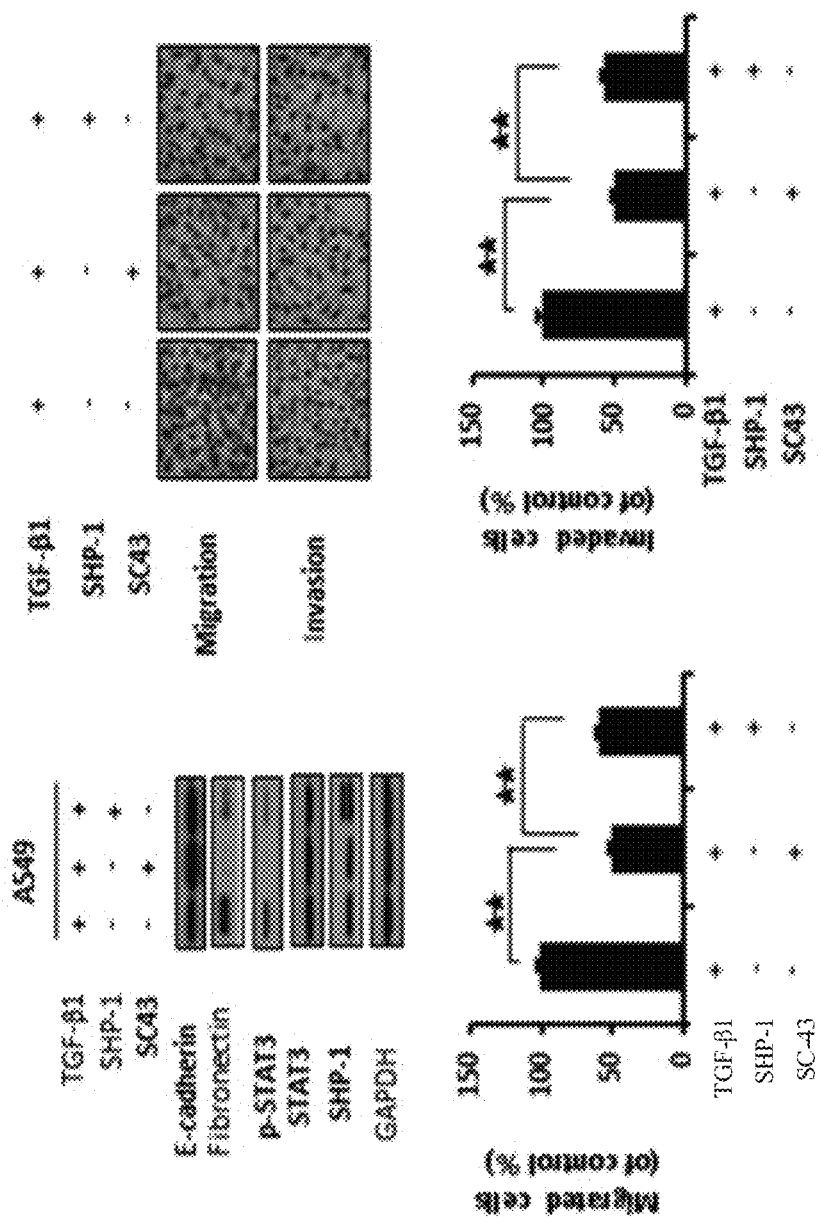
FIG. 9A shows the SHP-1 transfection in A549 cells
reduces the migration and invasion of cells which are the
markers of EMT.
Figure 9B:
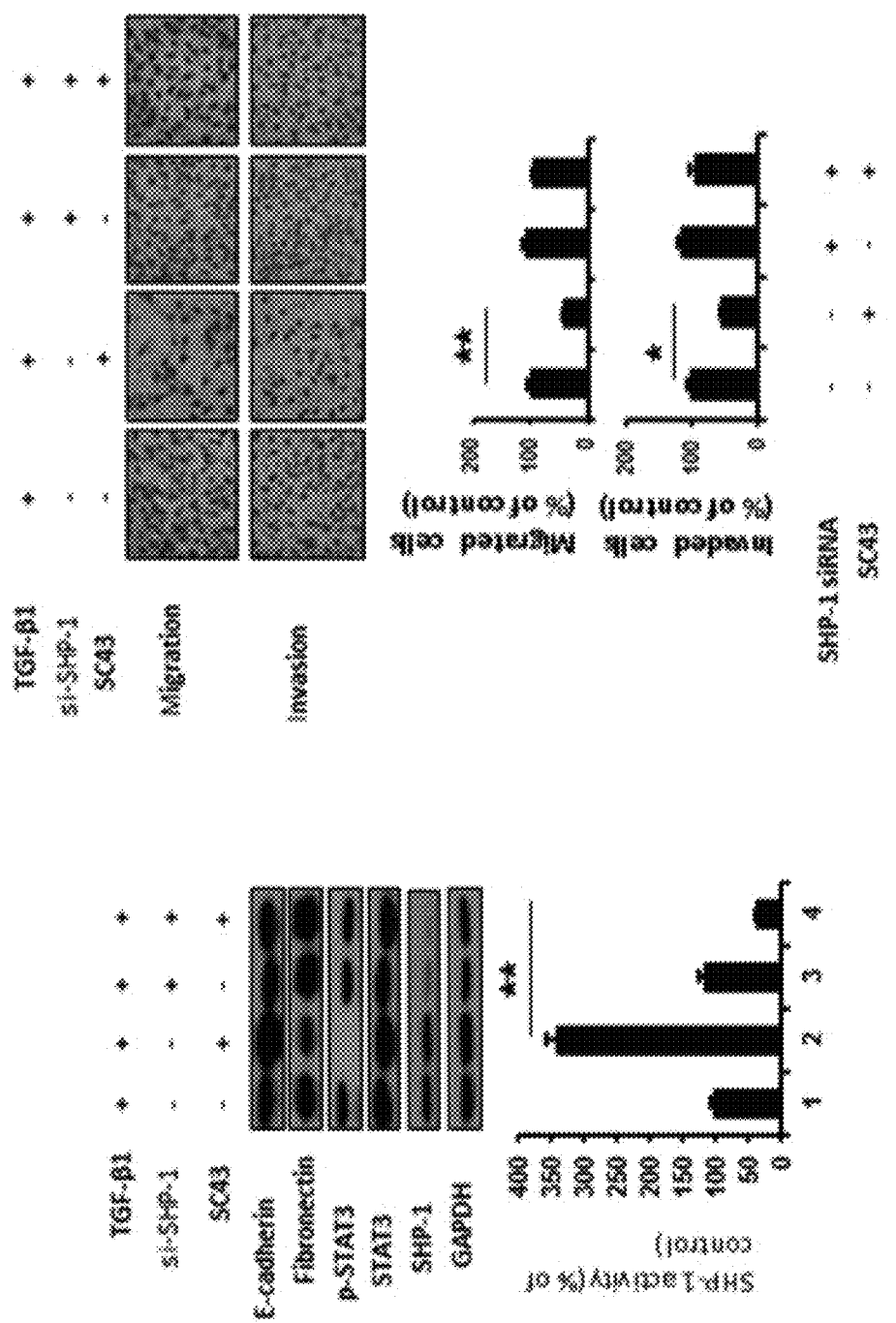
FIG. 9B shows the effects of the SHP-1 knockout by
siRNA in A549 cells on the migration and invasion of cells
which are the markers of EMT.
Figure 9C:
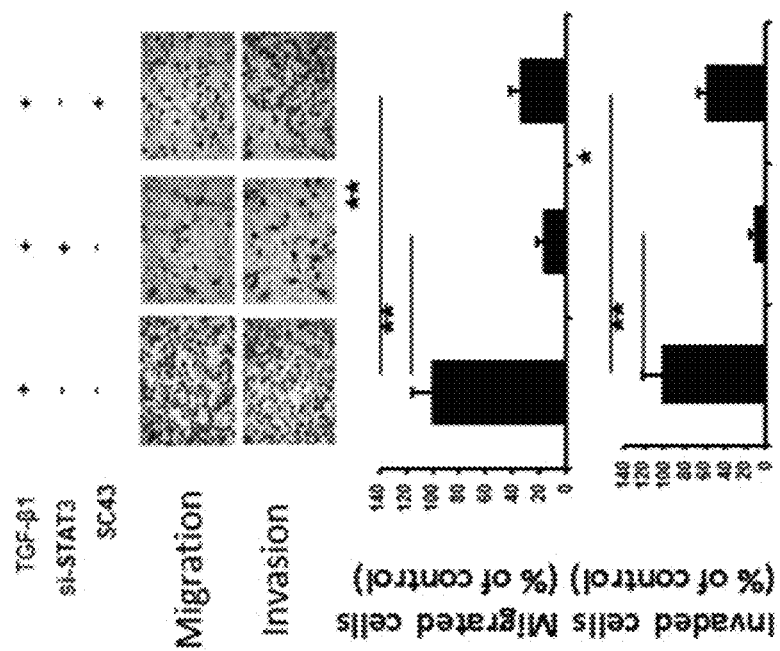
FIG. 9C shows the effects of the STAT3 knockout by
siRNA in A549 cells on the migration and invasion of cells
which are the markers of EMT.
Figure 9C:
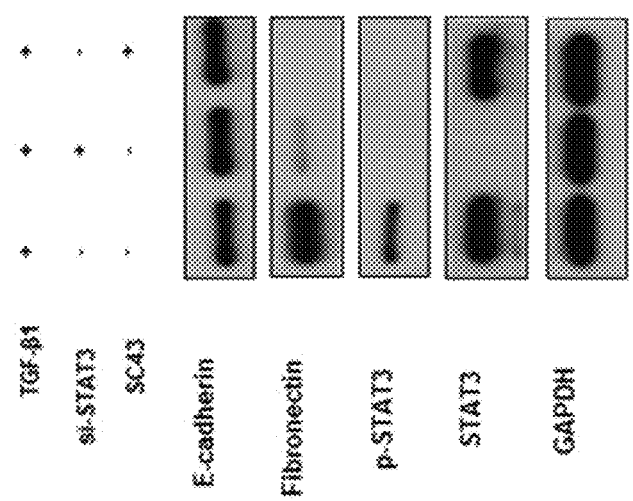

3.4 1-[4-chloro-3-(trifluoromethyl)phenyl]-3-[3-(4-cyanophenoxy)phenyl]urea Inhibits the Epithelial Mesenchymal Transition (EMT) by SHP-1/STAT3 Signaling Pathway To confirm the effect of 1-[4-chloro-3-(trifluoromethyl) phenyl]-3-[3-(4-cyanophenoxy)phenyl]urea on SHP-1/STAT3 signaling pathway, the present invention transfected SHP-1 in A549 cells, and the overexpression of SHP-1 would reduce the EMT marker, the migration, and the invasion of cells (FIG. 9A). The present invention then knocks out SHP-1 with siRNA to offset the effects of 1-[4-chloro-3-(trifluoromethyl)phenyl]-3-[3-(4-cyanophenoxy)phenyl]urea, including the expression of p-STAT3, the expression of EMT marker, the migration and the invasion of cells (FIG. 9B). These results indicated that 1-[4-chloro-3-(trifluoromethyl)phenyl]-3-[3-(4-cyanophenoxy)phenyl] urea inhibited EMT via controlling the activity of SHP-1, and downregulating the expression of p-STAT3 to reduce the epithelial mesenchymal transition in epithelial cells. Finally, the present invention knock out STAT3, which is a downstream molecule in the SHP-1/STAT3 signaling pathway, confirming that knocking out STAT3 offset the effects of 1-[4-chloro-3-(trifluoromethyl)phenyl]-3-[3-(4-cyanophenoxy)phenyl]urea, including the expression of EMT marker (FIG. 9C, left), the migration and the invasion of cells (FIG. 9C, right).

Therefore, the present invention demonstrates that 1-[4-chloro-3-(trifluoromethyl)phenyl]-3-[3-(4-cyanophenoxy)phenyl]urea treatment was effective in improving pulmonary fibrosis in a model of bleomycin-induced pulmonary fibrosis in mice. At the same time; in vitro studies showed that 1-[4-chloro-3-(trifluoromethyl)phenyl]-3-[3-(4-cyanophenoxy)phenyl]urea could inhibit epithelial mesenchymal transition (EMT) of epithelial cells, reduce the proliferation and the synthesis of collagen in fibroblasts, and promote fibroblast apoptosis. 1-[4-chloro-3-(trifluoromethyl)phenyl]-3-[3-(4-cyanophenoxy)phenyl]urea increased the activity of SHP-1 and inhibited STAT3 phosphorylation Enhanced the activity of SHP-1 significantly inhibited the EMT of epithelial cells and promoted the fibroblast apoptosis, whereas the inhibition of SHP-1 offset the EMT inhibition and the fibroblast apoptosis in epithelial cells induced by 1-[4-chloro-3-(trifluoromethyl)phenyl]-3-[3-(4-cyanophenoxy)phenyl]urea treatment. The present invent also found that 1-[4-chloro-3-(trifluoromethyl)phenyl]-3-[3-(4-cyanophenoxy)phenyl]urea interacted with the N—$SH_2$ domain of SHP-1 to enhance the activity of SHP-1 and inhibit the signal of STAT3, which were the mechanism of 1-[4-chloro-3-(trifluoromethyl)phenyl]-3-[3-(4-cyanophenoxy)phenyl]urea against fibrosis.

Example 4

Treatment of Reducing Hepatic Fibrosis in Mice by 1-[4-chloro-3-(trifluoromethyl)phenyl]-3-[3-(4-cyanophenoxy)phenyl]urea SHP-1 was overexpressed in the fibrotic region of human and mouse liver. The treatment of 1-[4-chloro-3-(trifluoromethyl)phenyl]-3-[3-(4-cyanophenoxy)-phenyl]urea in a mouse model, which was injected carbon tetrachloride ($CCl_4$) and bile duct ligation (BDL), could effectively prevent and reduce the hepatic fibrosis to improve the survival rate of the mice. In vitro studies have shown that 1-[4-chloro-3-(trifluoromethyl)phenyl]-3-[3-(4-cyanophenoxy)phenyl]urea promoted apoptosis of hepatic stellate cells (HSC); 1-[4-chloro-3-(trifluoromethyl)phenyl]-3-[3-(4-cyanophenoxy)phenyl]urea increased the activity of SHP-1, and inhibited the phosphorylation of STAT3, which was independent of the platelet-derived growth factor receptor pathway. Enhanced activity of SHP-1 significantly inhibited the proliferation of HSC, whereas the inhibition of SHP-1 offset 1-[4-chloro-3-(trifluoromethyl)phenyl]-3-[3-(4-cyanophenoxy)phenyl]urea-induced HSC apoptosis. In addition, 1-[4-chloro-3-(trifluoromethyl)phenyl]-3-[3-(4-cyanophenoxy)phenyl]urea interacted with the N—$SH_2$ domain of SHP-1 to increase the anti-fibrotic effect of SHP-1.

4.1 Relation Between the Phosphorylation of SHP-1 and Hepatic Fibrosis

Figure 10A:
FIG. 10A shows the expression level of SHP-1 phosphatase in CCl$_4$-induced hepatic fibrosis mouse model; scale
bar: 200 μm.
Figure 10B:
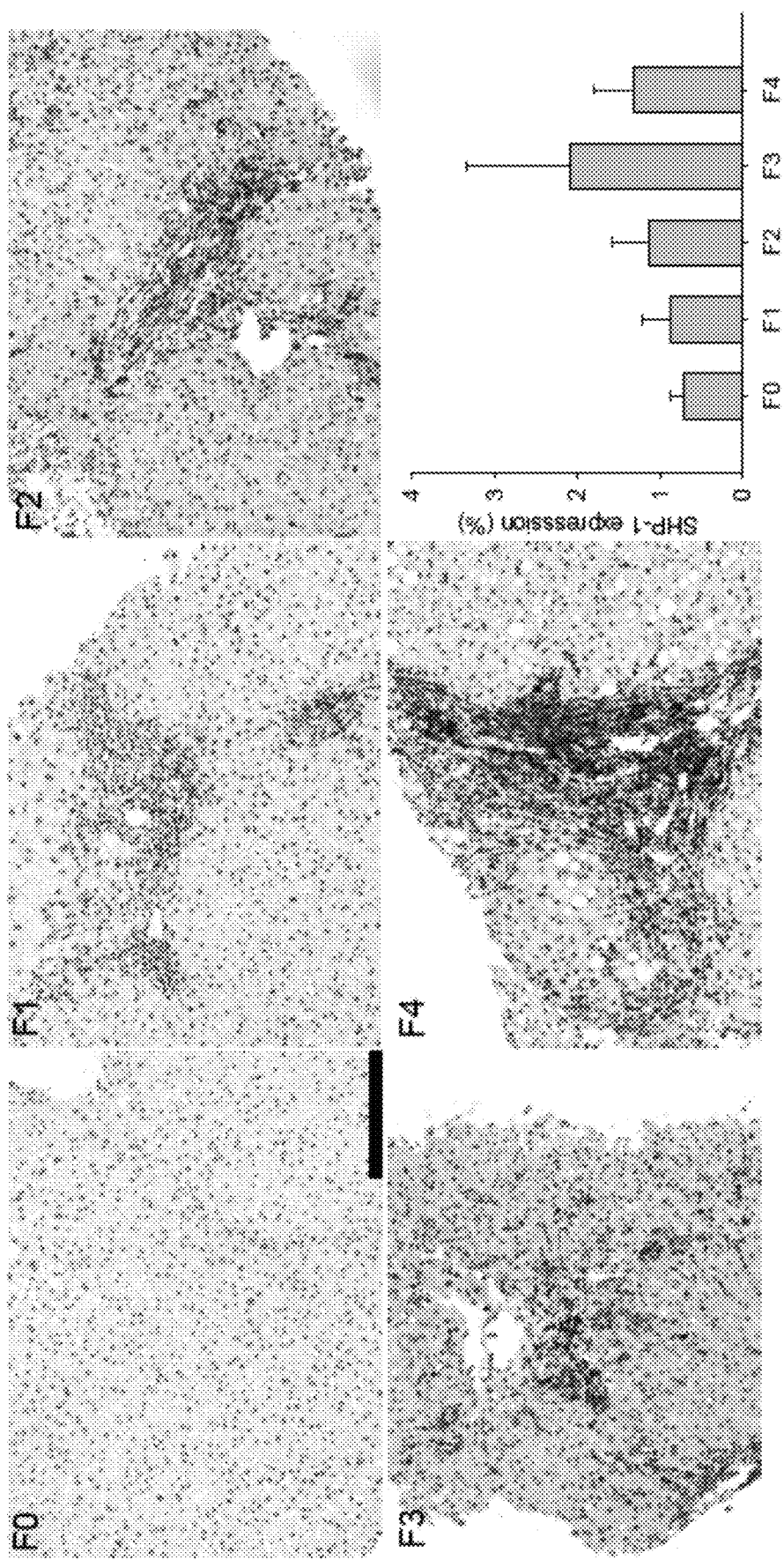
FIG. 10B shows the expression level of SHP-1 phosphatase in patients with chronic hepatitis B (CHB) advanced
fibrosis; scale bar: 200 μm.
Figure 10C:
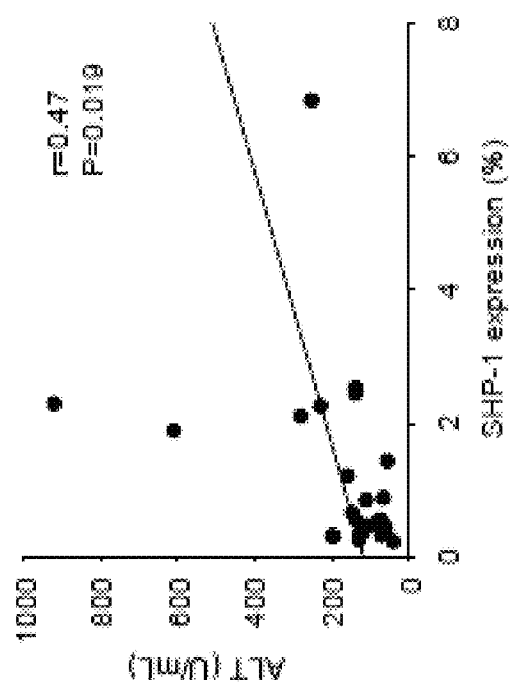
FIG. 10C shows the expression level of SHP-1 phosphatase is positive correlated with the concentration of
serum alanine aminotransferase (ALT).
Figure 10D:
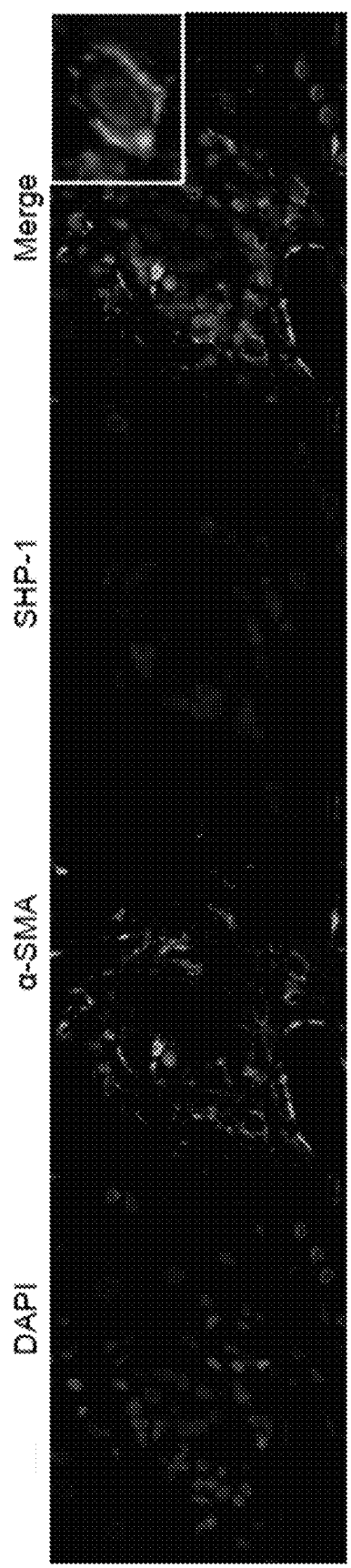
FIG. 10D shows the expression of SHP-1 phosphatase in
activated hepatic stellate cells (HSC). SHP-1 phosphatase is
colocalized with the activated hepatic stellate cell marker,
α-SMA, confirming that SHP-1 phosphatase is expressed in
activated hepatic stellate cells.

Therefore, the present invention investigated the expression of SHP-1, which was the inhibitor of P-STAT3, in fibrotic liver. In the hepatic fibrosis mouse model which was induced by $CCl_4$ for 4 weeks, SHP-1 was overexpressed in regions with significant fibrosis (FIG. 10A). The present invention further investigates the expression of SHP-1 in patients with chronic hepatitis B (CHB) with various degrees of fibrosis, and the expression of SHP-1 in patients with advanced fibrosis was significantly increased (FIG. 10B). The expression of SHP-1 was positively correlated with the concentration of serum alanine aminotransferase (ALT) (FIG. 10C). SHP-1 was colocalized with the activated HSC marker, α-SMA (FIG. 10D). These data suggested that SHP-1 involved in the development of hepatic fibrosis.

Figure 11A:
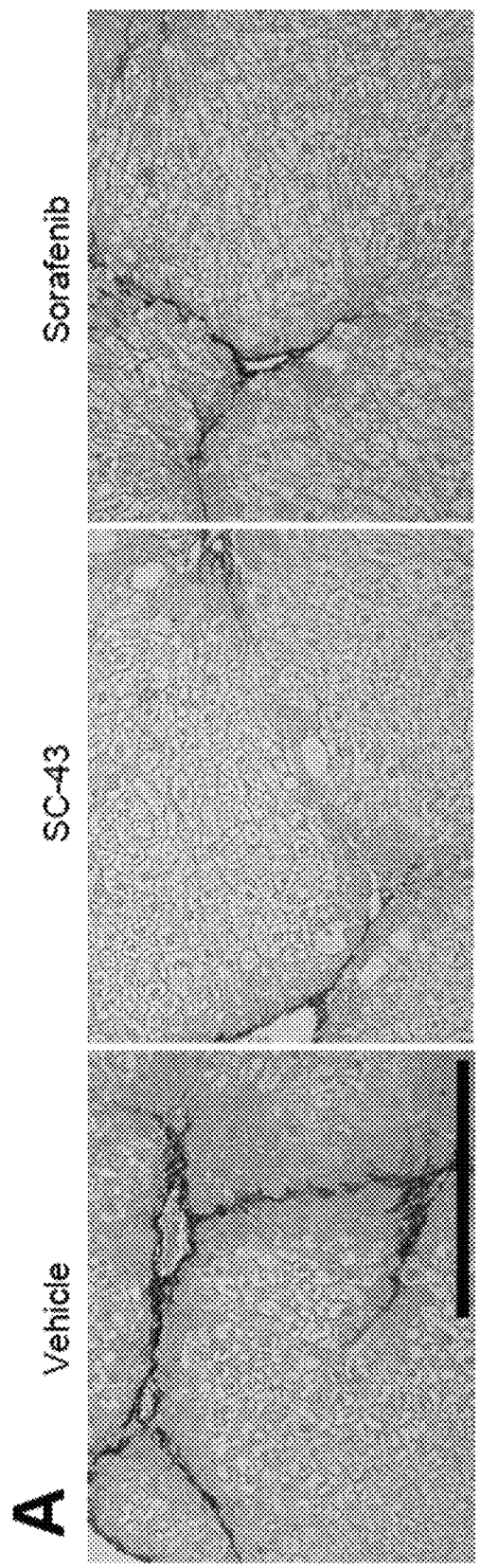
FIG. 11A shows the picrosirius red stain images of
improving the hepatic fibrosis by 1-[4-chloro-3-(trifluoromethyl)phenyl]-3-[3-(4-cyanophenoxylphenyl]urea in CCl$_4$-induced hepatic fibrosis mice prevention model; n=7-9 for each cohort.
Figure 11B:
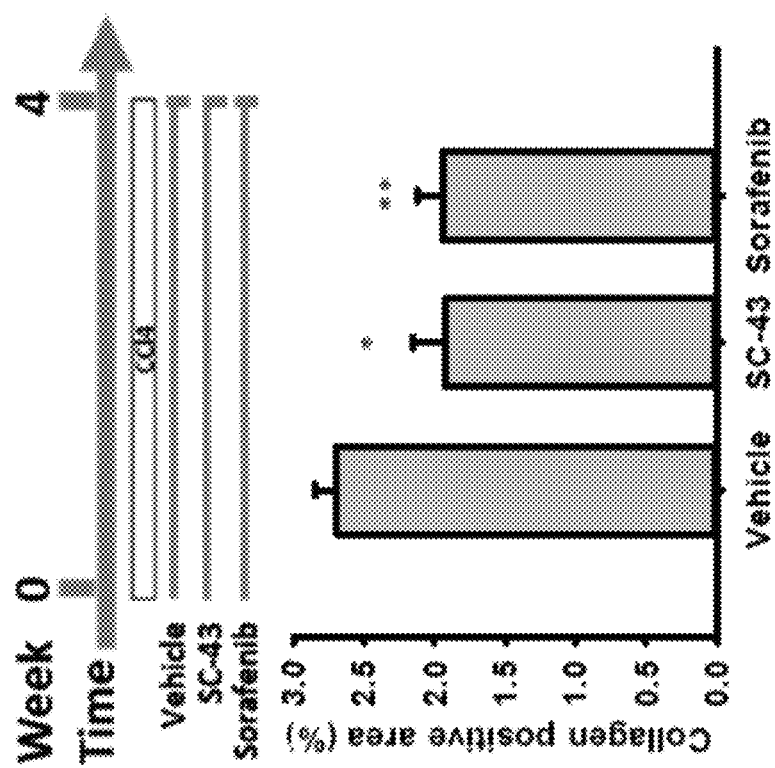
FIG. 11B shows the graph of quantitative collagen-positive area (qCPA) measured by photodensitization of the picrosirius red stain images of improving the hepatic fibrosis by 1-[4-chloro-3-(trifluoromethyl)phenyl]-3-[3-(4-cyanophenoxy)-phenyl]urea in CCl$_4$-induced hepatic fibrosis mice prevention model; the column represents the mean, and the error bar represents the standard deviation; *P<0.05, P<0.01, and *P<0.001 compared to vehicle, and n=7-9 for each group.
Figure 11C:
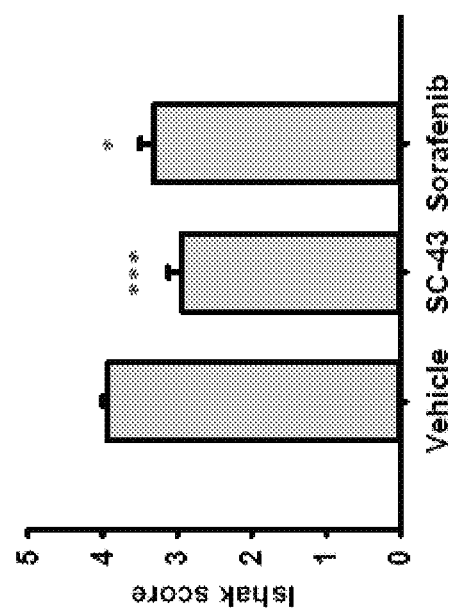
FIG. 11C shows the Ishak fibrosis score grading data of improving the hepatic fibrosis by 1-[4-chloro-3-(trifluoromethyl)phenyl]-3-[3-(4-cyanophenoxy)-phenyl]urea in CCl$_4$-induced hepatic fibrosis mice prevention model; the column represents the mean, and the error bar represents the standard deviation; *P<0.05, P<0.01, and *P<0.001 compared to vehicle, and n=7-9 for each group.
Figure 11D:
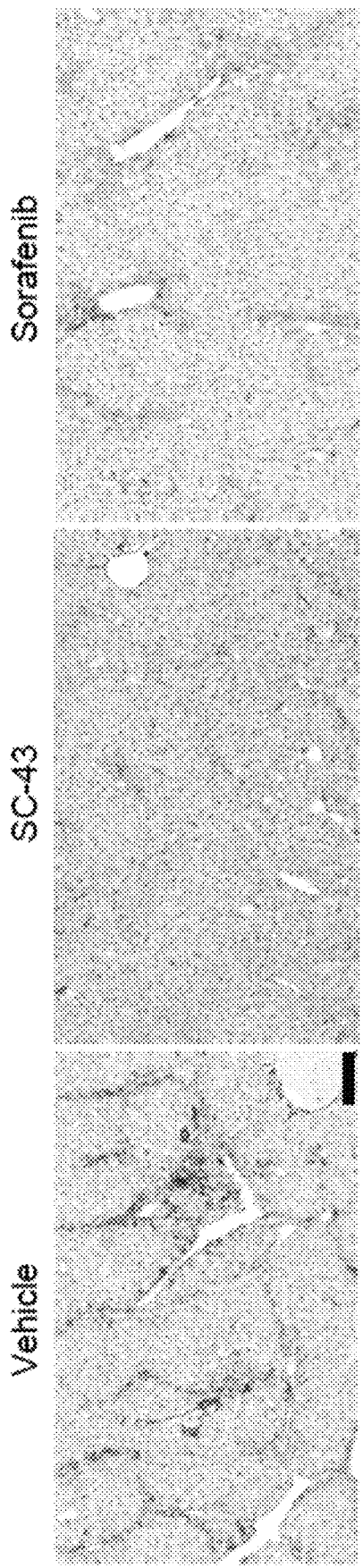
FIG. 11D shows the α-SMA stain images of improving the hepatic fibrosis by 1-[4-chloro-3-(trifluoromethyl)phenyl]-3-[3-(4-cyanophenoxy)phenyl]urea in CCl$_4$-induced hepatic fibrosis mice prevention model. α-SMA is the activated hepatic stellate cell marker; scale bar: 200 µm; n=7-9 for each cohort.
Figure 11E:
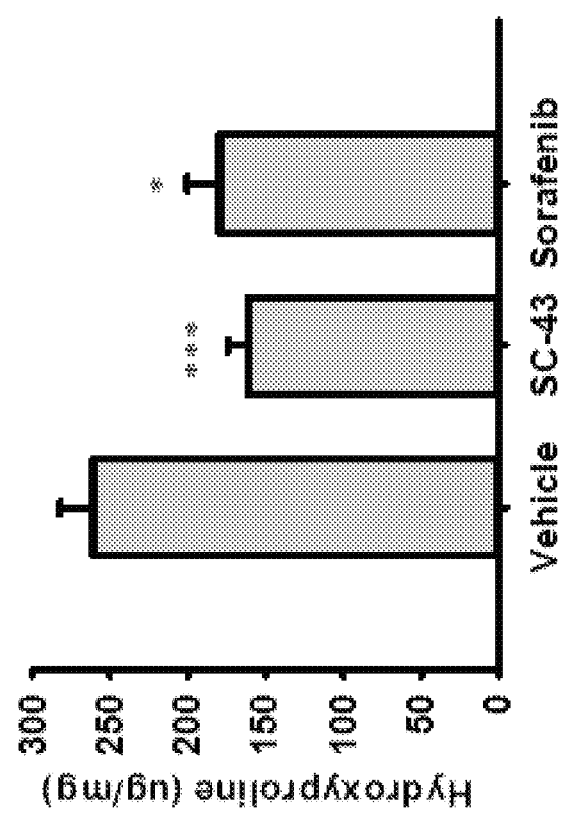
FIG. 11E shows the hydroxyproline concentration of improving the hepatic fibrosis by 1-[4-chloro-3-(trifluoromethyl)phenyl]-3-[3-(4-cyanophenoxy)phenyl]urea in CCl$_4$-induced hepatic fibrosis mice prevention model; the column represents the mean, and the error bar represents the standard deviation; *P<0.05, P<0.01, and *P<0.001 compared to vehicle, and n=7-9 for each group.

4.2 Improvement of Fibrosis in $CCl_4$-Induced Hepatic Mouse Model by 1-[4-chloro-3-(trifluoromethyl)phenyl]-3-[3-(4-cyanophenoxy)phenyl]urea The present inventors have demonstrated that 1-[4-chloro-3-(trifluoromethyl)phenyl]-3-[3-(4-cyanophenoxy)phenyl]urea in enhancing SHP-1 activity was better than the known anti-fibrosis drug sorafenib (FIG. 2A). Therefore, we hypothesized that 1-[4-chloro-3-(trifluoromethyl)phenyl]-3-[3-(4-cyanophenoxy)-phenyl]urea has a more favorable anti-fibrotic activity than does sorafenib. In the fibrosis mice prevention model, 1-[4-chloro-3-(trifluoromethyl)phenyl]-3-[3-(4-cyanophenoxy)phenyl]urea and sorafenib were concurrently administered with $CCl_4$ for 4 weeks. Following the 1-[4-chloro-3-(trifluoromethyl)phenyl]-3-[3-(4-cyanophenoxy)phenyl]urea and sorafenib treatment, significant fibrosis regression was observed through Picrosirius Red staining (FIG. 11A), the qCPA measured by photodensitization (FIG. 11B), the Ishak fibrosis score (FIG. 11C), α-SMA expression, (FIG. 11D), and the hydroxyproline concentration (FIG. 11E).

Figure 12A:
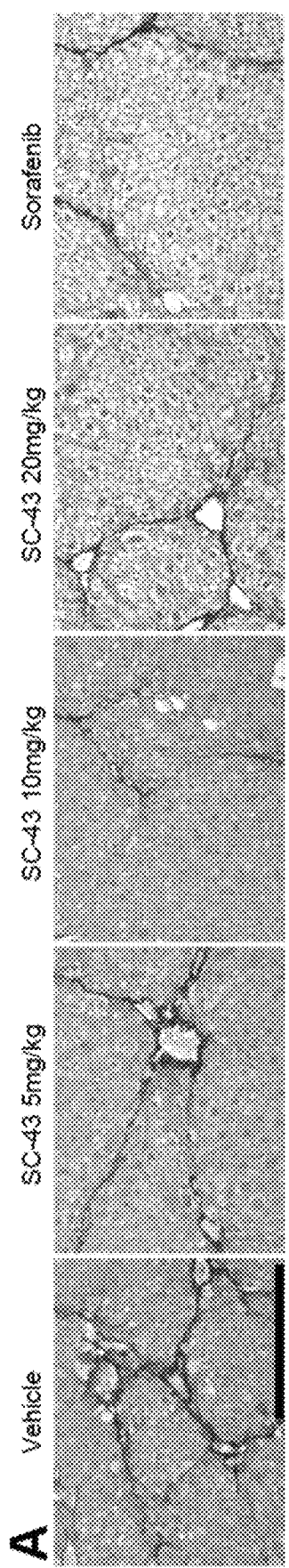
FIG. 12A shows the picrosirius red stain images of improving the hepatic fibrosis by 1-[4-chloro-3-(trifluoromethyl)phenyl]-3-[3-(4-cyanophenoxy)phenyl]urea in CCl$_4$-induced hepatic fibrosis mice treatment model; scale bar: 200 µm; n=6-8 for each cohort.
Figure 12B:
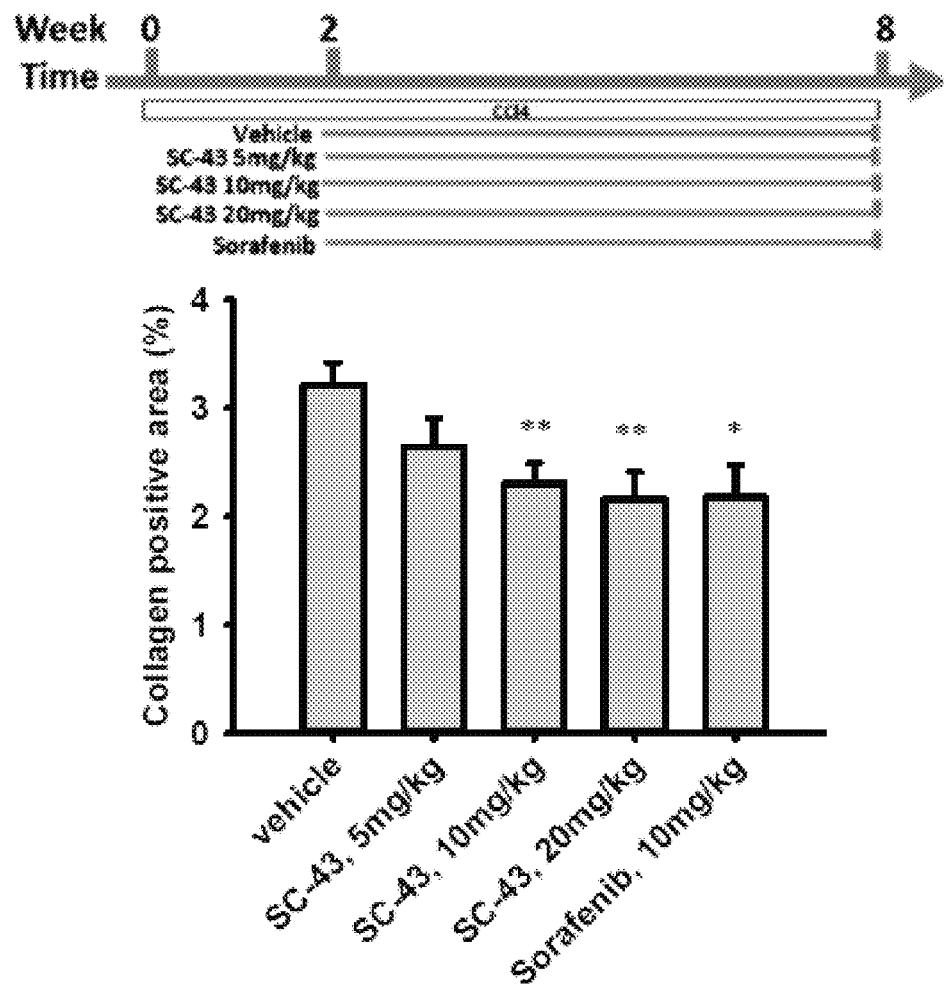
FIG. 12B shows the graph of quantitative collagen-positive area (qCPA) measured by photodensitization of the picrosirius red stain images of improving the hepatic fibrosis by 1-[4-chloro-3-(trifluoromethyl)phenyl]-3-[3-(4-cyanophenoxy)-phenyl]urea in CCl$_4$-induced hepatic fibrosis mice treatment model; the column represents the mean, and the error bar represents the standard deviation; *P<0.05, P<0.01, and *P<0.001 compared to vehicle, and n=6-8 for each group.
Figure 12C:
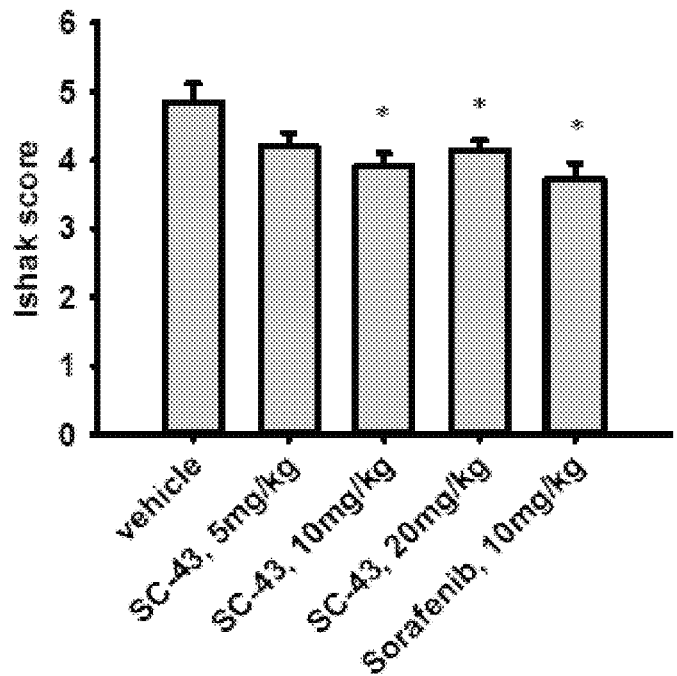
FIG. 12C shows the Ishak fibrosis score grading data of improving the hepatic fibrosis by 1-[4-chloro-3-(trifluoromethyl)phenyl]-3-[3-(4-cyanophenoxy)-phenyl]urea in CCl$_4$-induced hepatic fibrosis mice treatment model; the column represents the mean, and the error bar represents the standard deviation; *P<0.05, P<0.01, and *P<0.001 compared to vehicle, and n=6-8 for each group.
Figure 12D:
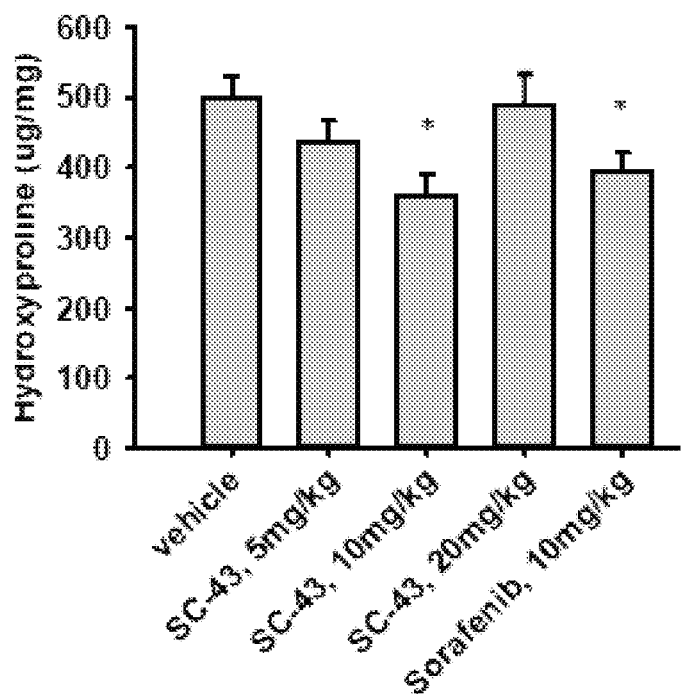
FIG. 12D shows the hydroxyproline concentration of improving the hepatic fibrosis by 1-[4-chloro-3-(trifluoromethyl)phenyl]-3-[3-(4-cyanophenoxy)phenyl]urea in CCl$_4$-induced hepatic fibrosis mice treatment model; the column represents the mean, and the error bar represents the standard deviation; *P<0.05, P<0.01, and *P<0.001 compared to vehicle, and n=6-8 for each group.
Figure 12E:
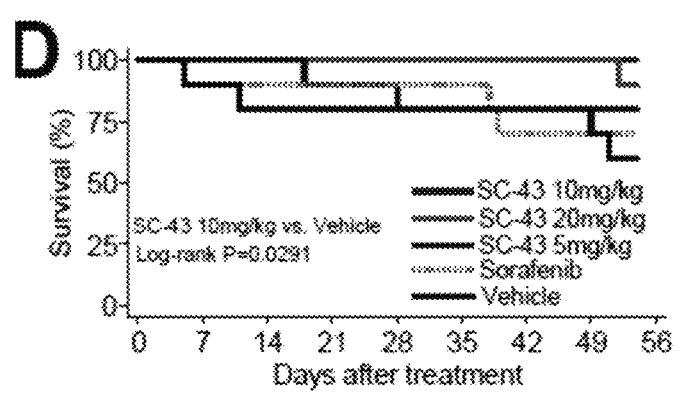
FIG. 12E shows the treatment of 1-[4-chloro-3-(trifluoromethyl)phenyl]-3-[3-(4-cyanophenoxy)phenyl]urea improves the survival rate (log-rank P=0.0291) of mice with hepatic fibrosis in CCl$_4$-induced hepatic fibrosis mice treatment model; n=6-10 for each group.

In the hepatic fibrosis mice treatment model, mild hepatic fibrosis (Ishak score, 2-3) was achieved after $CCl_4$ induction for 2 weeks. 1-[4-chloro-3-(trifluoromethyl)phenyl]-3-[3-(4-cyanophenoxy)phenyl]urea (5, 10, or 20 mg/kg) or sorafenib (10 mg/kg) were concurrently administered with $CCl_4$ in the following 6 weeks. 1-[4-chloro-3-(trifluoromethyl)phenyl]-3-[3-(4-cyanophenoxy)-phenyl]urea and sorafenib treatment significantly improved hepatic fibrosis, as observed through the picrosirius red staining (FIG. 12A). An increasing anti-fibrotic activity of 1-[4-chloro-3-(trifluoromethyl)phenyl]-3-[3-(4-cyanophenoxy)phenyl]urea was observed in the qCPA measured by photodensitization (FIG. 12B), Ishak fibrosis score (FIG. 12C), and the hydroxyproline concentration (FIG. 12D). Furthermore, the 1-[4-chloro-3-(trifluoromethyl)phenyl]-3-[3-(4-cyanophenoxy)phenyl] urea (10 mg/kg) treatment significantly improved the survival rate compared with the control group (log-rank P=0.0291) and a tendency to yield higher survival than the sorafenib treatment (log rank P=0.0671; FIG. 12E).

Figure 12F:
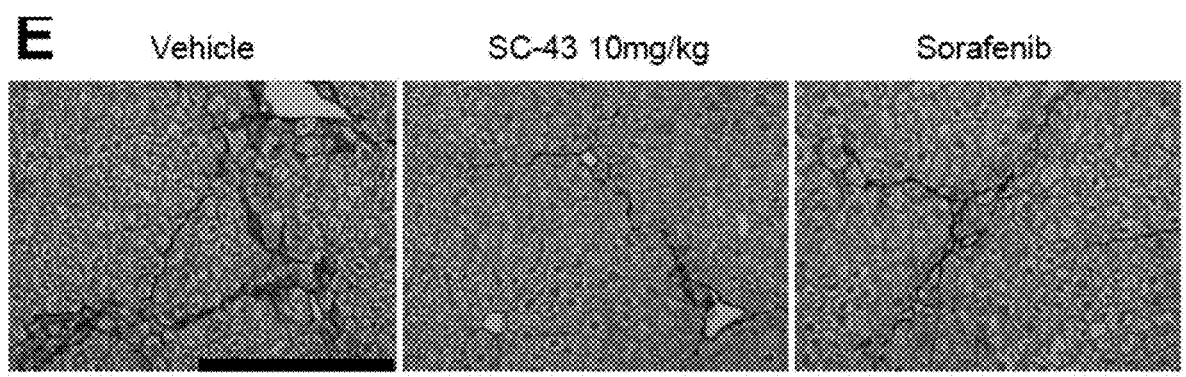
FIG. 12F shows the picrosirius red stain images of improving the hepatic fibrosis by 1-[4-chloro-3-(trifluoromethyl)phenyl]-3-[3-(4-cyanophenoxy)phenyl]urea in CCl$_4$-induced hepatic fibrosis mice regression model; scale bar: 200 µm; n=6-8 for each cohort.
Figure 12G:
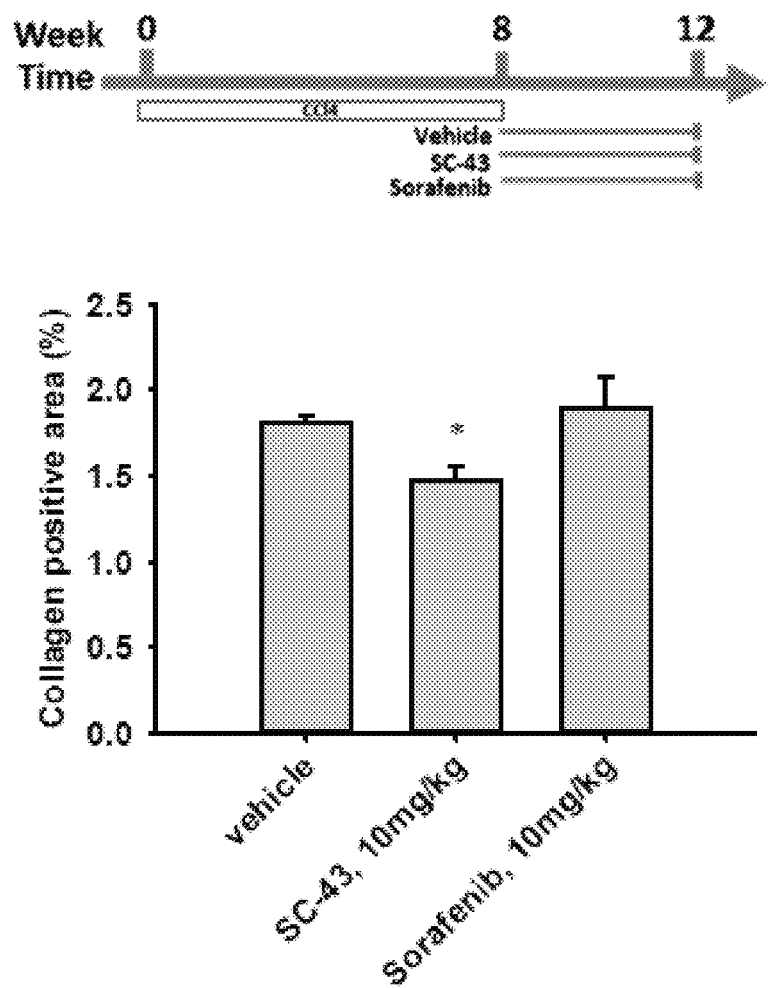
FIG. 12G shows the graph of quantitative collagen-positive area (qCPA) measured by photodensitization of the picrosirius red stain images of improving the hepatic fibrosis by 1-[4-chloro-3-(trifluoromethyl)phenyl]-3-[3-(4-cyanophenoxy)-phenyl]urea in CCl$_4$-induced hepatic fibrosis mice regression model; the column represents the mean, and the error bar represents the standard deviation; *P<0.05, P<0.01, and *P<0.001 compared to vehicle, and n=6-8 for each group.
Figure 12H:
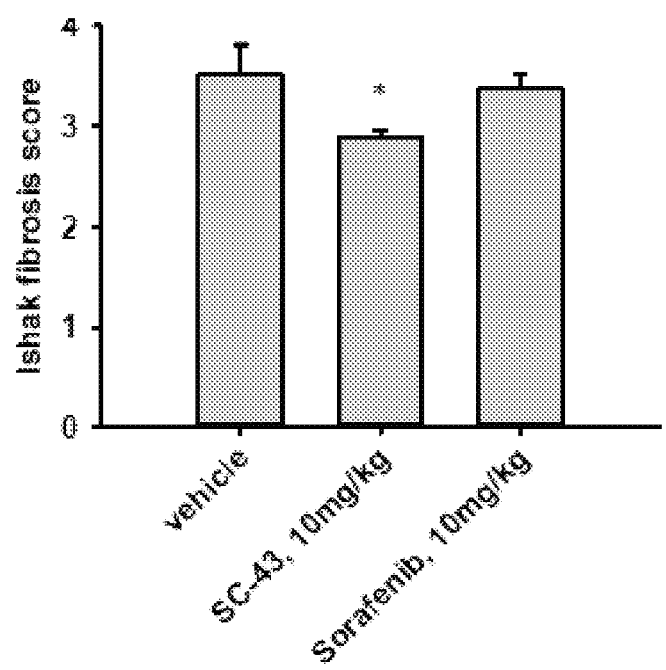
FIG. 12H shows the Ishak fibrosis score grading data of improving the hepatic fibrosis by 1-[4-chloro-3-(trifluoromethyl)phenyl]-3-[3-(4-cyanophenoxy)-phenyl]urea in CCl$_4$-induced hepatic fibrosis mice regression model; the column represents the mean, and the error bar represents the standard deviation; *P<0.05, P<0.01, and *P<0.001 compared to vehicle, and n=6-8 for each group.

In the fibrosis mice regression model, advanced fibrosis and cirrhosis (Ishak score, 4-6) was developed through $CCl_4$ induction for 8 weeks. 1-[4-chloro-3-(trifluoromethyl)phenyl]-3-[3-(4-cyanophenoxy)phenyl]urea (10 mg/kg) and sorafenib (10 mg/kg) were administered for the following 4 weeks without $CCl_4$. At sacrifice, we observed that hepatic fibrosis improved even in the control group (FIG. 12F, compared with FIG. 12A), indicating spontaneous fibrosis regression after discontinuing $CCl_4$ induction for 8 weeks. However, we observed a significantly decreased qCPA and Ishak fibrosis score in the 1-[4-chloro-3-(trifluoromethyl)phenyl]-3-[3-(4-cyanophenoxy)phenyl]urea treatment group (FIG. 12G and FIG. 12H).

Figure 13A:
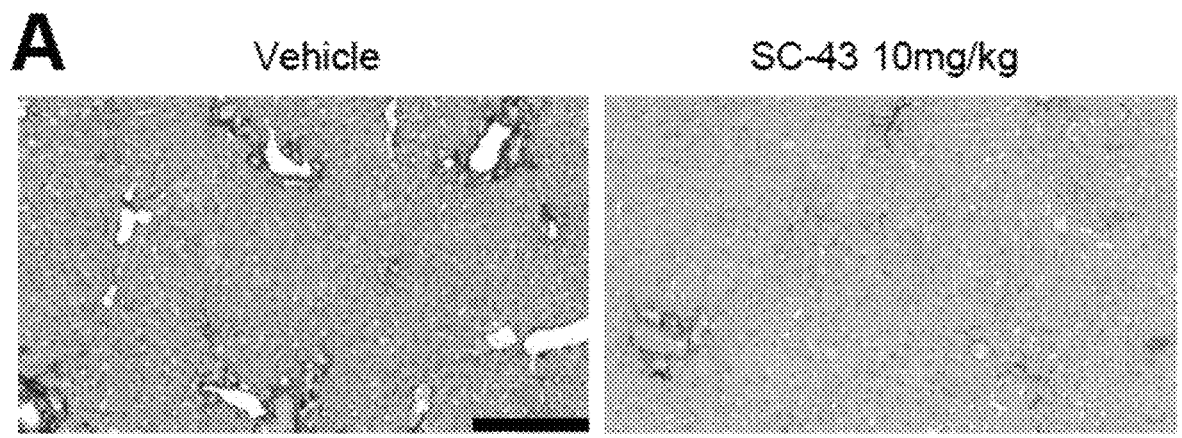
FIG. 13A shows the picrosirius red slain images of improving the hepatic fibrosis by 1-[4-chloro-3-(trifluoromethyl)phenyl]-3-[3-(4-cyanophenoxy)phenyl]urea in the bile duct ligation (BDL) mice prevention model; scale bar: 200 µm; n=7-8 for each cohort.
Figure 13B:
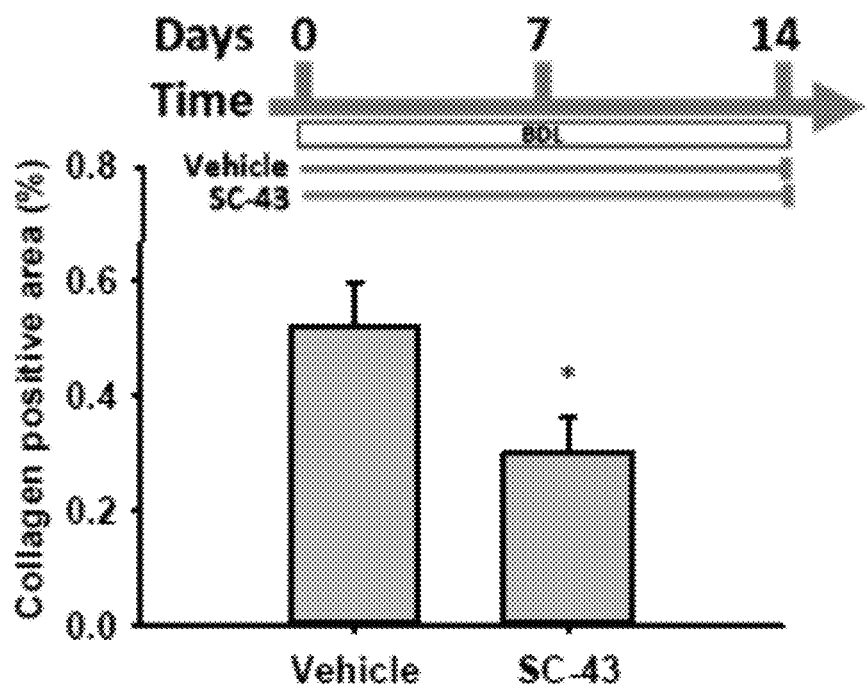
FIG. 13B shows the graph of quantitative collagen-positive area (qCPA) measured by photodensitization of the picrosirius red stain images of improving the hepatic fibrosis by 1-[4-chloro-3-(trifluoromethyl)phenyl]-3-[3-(4-cyanophenoxy)-phenyl]urea in BDL-induced cholestasis fibrosis mice prevention model; the column represents the mean, and the error bar represents the standard deviation; *P<0.05, P<0.01, and *P<0.001 compared to vehicle, and n=7-8 for each group.

4.3 1-[4-chloro-3-(trifluoromethyl)phenyl]-3-[3-(4-cyanophenoxy)phenyl]urea Treatment Improves Hepatic Fibrosis in the Bile Duct Ligation Liver Fibrosis Mouse Model We further investigated the anti-fibrotic activity of 1-[4-chloro-3-(trifluoromethyl)phenyl]-3-[3-(4-cyanophenoxy)

phenyl]urea in the bile duct ligation (BDL) model. In the fibrosis mice prevention model, the vehicle and 1-[4-chloro-3-(trifluoromethyl)phenyl]-3-[3-(4-cyanophenoxy)phenyl]urea (10 mg/kg) were administered from day 1 until sacrifice on day 14 of BDL. The 1-[4-chloro-3-(trifluoromethyl)phenyl]-3-[3-(4-cyanophenoxy)phenyl]urea treatment significantly reduced the quantitative collagen-positive area (qCPA) measured by photodensitization of the picrosirius red stain images. (FIG. 13A and FIG. 13B).

Figure 13C:
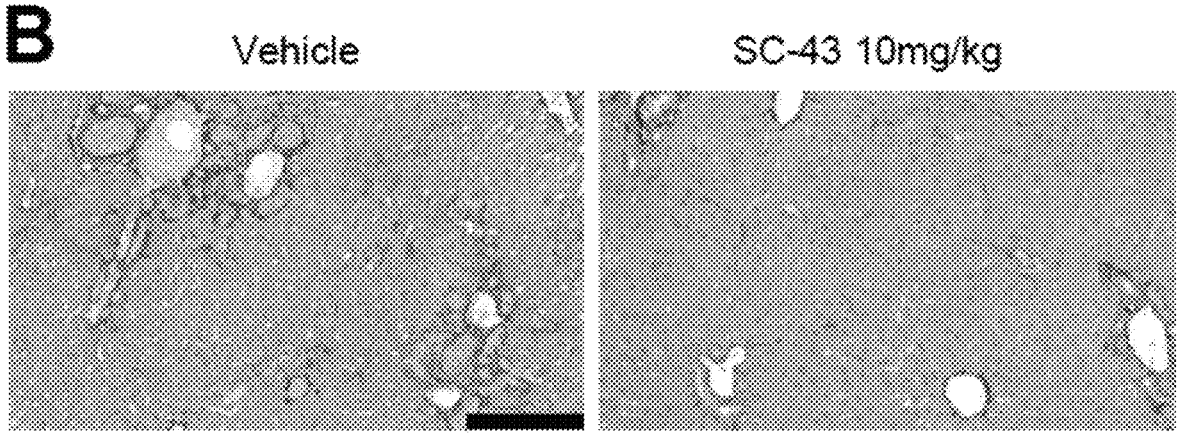
FIG. 13C shows the picrosirius red stain images of improving the hepatic fibrosis by 1-[4-chloro-3-(trifluoromethyl)phenyl]-3-[3-(4-cyanophenoxy)phenyl]urea in BDL-induced cholestasis fibrosis mice treatment model; scale bar: 200 µm; n=7-8 for each cohort.
Figure 13D:
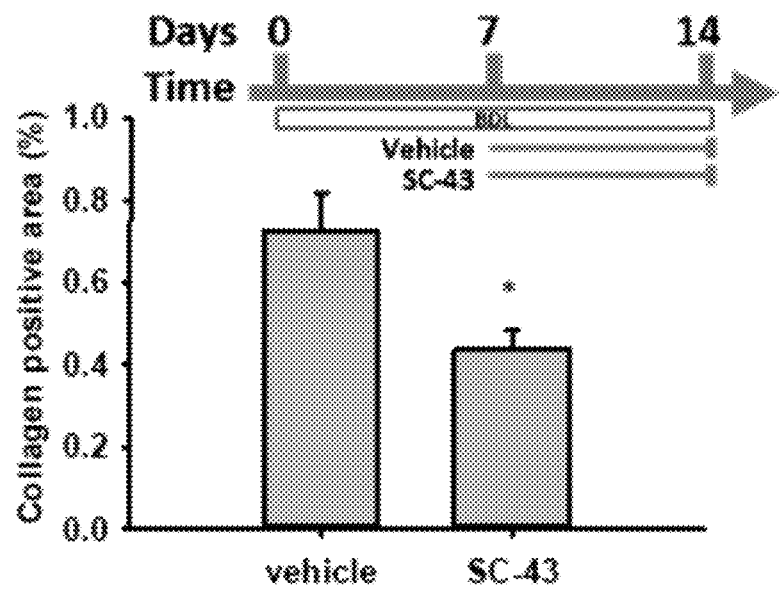
FIG. 13D shows the graph of quantitative collagen-positive area (qCPA) measured by photodensitization of the picrosirius red stain images of improving the hepatic fibrosis by 1-[4-chloro-3-(trifluoromethyl)phenyl]-3-[3-(4-cyanophenoxy)-phenyl]urea in BDL-induced cholestasis fibrosis mice treatment model; the column represents the mean, and the error bar represents the standard deviation; *P<0.05, P<0.01, and *P<0.001 compared to vehicle, and n=7-8 for each group.

In the fibrosis mice treatment model, the vehicle and 1-[4-chloro-3-(trifluoromethyl)phenyl]-3-[3-(4-cyanophenoxy)phenyl]urea (10 mg/kg) were administered from day 8 until sacrifice on day 14 following BDL. The 1-[4-chloro-3-(trifluoromethyl)phenyl]-3-[3-(4-cyanophenoxy)phenyl]urea treatment significantly reduced the quantitative collagen-positive area (qCPA) measured by photodensitization of the picrosirius red stain images. (FIG. 13C and FIG. 13D). These results suggested the anti-fibrotic activity of 1-[4-chloro-3-(trifluoromethyl)-phenyl]-3-[3-(4-cyanophenoxy)phenyl]urea in the prevention, treatment, and regression of hepatic fibrosis.

4.4 1-[4-chloro-3-(trifluoromethyl)phenyl]-3-[3-(4-cyanophenoxy)phenyl]urea Induces the Apoptosis of Hepatic Stellate Cells Through Platelet-Derived Growth Factor Receptor (PDGFR)-Dependent Signal Transducer and Activator of Transcription 3 (STAT3)

The anti-fibrotic mechanism of 1-[4-chloro-3-(trifluoromethyl)phenyl]-3-[3-(4-cyanophenoxy)phenyl]urea was further investigated in vitro. The 1-[4-chloro-3-(trifluoromethyl)phenyl]-3-[3-(4-cyanophenoxy)phenyl]urea treatment had dose-dependent effects to reduce the viability of HSC-T6 cells and LX2 cells, more significant than sorafenib; the 1-[4-chloro-3-(trifluoromethyl)phenyl]-3-[3-(4-cyanophenoxy)phenyl]urea treatment also exerted dose- and time-dependent effects to reduce the viability of primary mouse HSCs (FIG. 14A). In addition, compared with sorafenib, 1-[4-chloro-3-(trifluoromethyl)phenyl]-3-[3-(4-cyanophenoxy)phenyl]urea significantly increased HSC apoptosis in a dose-dependent manner (FIG. 14B). Western blotting revealed that 1-[4-chloro-3-(trifluoromethyl)phenyl]-3-[3-(4-cyanophenoxy)phenyl]urea dose-dependently increased the cleavage of poly(ADP-ribose) polymerase (PARP) fragments (FIG. 14C).

Since transforming growth factor (TGF)-β and PDGFR were the major canonical pathways involved in fibrogenesis, HSC activation, and proliferation, we first investigated the effects of 1-[4-chloro-3-(trifluoromethyl)phenyl]-3-[3-(4-cyanophenoxy)phenyl]urea on TGF-β and PDGFR pathways. 1-[4-chloro-3-(trifluoromethyl)phenyl]-3-[3-(4-cyanophenoxy)phenyl]urea downregulated p-Smad2 and p-Smad3 of the TGF-β pathway in LX2 cells (FIG. 14D). It also downregulated p-PDGFR and p-Akt in the PDGFR pathway both in HSC-T6 cells and LX2 cells (FIG. 14E).

We further investigated the effects of 1-[4-chloro-3-(trifluoromethyl)phenyl]-3-[3-(4-cyanophenoxy)phenyl]urea on the STAT3 pathway, which was a key regulator of fibrogenesis. The 1-[4-chloro-3-(trifluoromethyl)phenyl]-3-[3-(4-cyanophenoxy)phenyl]urea treatment showed more significant dose-escalation effects on the downregulation of p-STAT3 and cyclin D1 in LX2 cells and HSC-T6 cells than did sorafenib (FIG. 15A). 1-[4-chloro-3-(trifluoromethyl)phenyl]-3-[3-(4-cyanophenoxy)phenyl]urea also suppressed the IL-6-induced p-STAT3 upregulation (FIG. 15B). Moreover, 1-[4-chloro-3-(trifluoromethyl)phenyl]-3-[3-(4-cyanophenoxy)phenyl]urea-induced apoptosis was significantly abolished in STAT3-overexpressing HSCs (FIG. 15C). These results suggested that 1-[4-chloro-3-(trifluoromethyl)phenyl]-3-[3-(4-cyanophenoxy)phenyl]urea induced HSC apoptosis more significantly than sorafenib through the inhibition of STAT3 pathway.

In addition, after administering AG1295, a specific PDGFR inhibitor, we observed that 1-[4-chloro-3-(trifluoromethyl)phenyl]-3-[3-(4-cyanophenoxy)-phenyl]urea still downregulated p-Akt and p-STAT3, independent of the PDGFR signaling (FIG. 15D). This result suggested that 1-[4-chloro-3-(trifluoromethyl)-phenyl]-3-[3-(4-cyanophenoxy)phenyl]urea and PDGFR independently down-regulate p-Akt and p-STAT3 signaling, both of which were involved in cell proliferation and survival.

4.5 SHP-1 Plays a Crucial Role in 1-[4-chloro-3-(trifluoromethyl)-phenyl]-3-[3-(4-cyanophenoxy)phenyl]urea Induced STAT3 Inhibition SHP-1 contained two $SH_2$ domains at the N-terminus (N—$SH_2$ and C—$SH_2$), followed by a catalytic protein tyrosine phosphatase (PTPase) domain and C-terminal tail. In its inactive form, the D61 site at the N—$SH_2$ domain interacted with the WPD site on the PTPase domain and hinders its PTPase activity. The SHP-1 activity increased in dN1 and D61A mutants (FIG. 16A).

To investigate the role of SHP-1 in HSC apoptosis, we observed that SHP-1 overexpression significantly reduced cell viability since day 2 of the transfection (FIG. 16B). Compared with sorafenib, the 1-[4-chloro-3-(trifluoromethyl)phenyl]-3-[3-(4-cyanophenoxy)phenyl]urea treatment significantly increased the SHP-1 activity at a lower concentration both in LX2 cells and HSC-T6 cells (FIG. 16C). In addition, the inhibition of SHP-1 by vanadate, a nonspecific phosphatase inhibitor, rescued the 1-[4-chloro-3-(trifluoromethyl)phenyl]-3-[3-(4-cyanophenoxy)phenyl]-urea-induced apoptosis of LX2 cells through p-STAT3 upregulation (FIG. 16D). Similarly, an SHP-1 specific inhibitor, PTP inhibitor III, also upregulated p-STAT3 and rescued the 1-[4-chloro-3-(trifluoromethyl)phenyl]-3-[3-(4-cyanophenoxy)phenyl]urea-induced apoptosis of LX2 cells (FIG. 16E). The anti-proliferative activity of 1-[4-chloro-3-(trifluoromethyl)phenyl]-3-[3-(4-cyanophenoxy)phenyl]urea was significantly counteracted by SHP-1 knockdown by using siRNA (FIG. 16F), suggesting that 1-[4-chloro-3-(trifluoromethyl)phenyl]-3-[3-(4-cyanophenoxy)-phenyl]urea mainly targets SHP-1 and HSC proliferation was considerably affected by SHP-1 expression and activity.

These results suggest that SHP-1 activation reduced HSC proliferation. The 1-[4-chloro-3-(trifluoromethyl)phenyl]-3-[3-(4-cyanophenoxy)phenyl]urea treatment increased the SHP-1 activity and downregulated p-STAT3 to promote HSC apoptosis, whereas SHP-1 inhibition counteracted the effects of 1-[4-chloro-3-(trifluoromethyl)phenyl]-3-[3-(4-cyanophenoxy)phenyl]urea.

4.6 Expression of SHP-1 Mutants and Proliferation of HSCs

The associations of the ectopic expression of wild-type SHP-1, dN1, and D61A with HSC proliferation were further examined using a colony formation assay. As shown in FIG. 17A, the ectopic expression of SHP-1, dN1, and D61A significantly inhibited the number of colonies compared with the vector control. In addition, dN1 and D61A expression significantly reduced the cell viability, as observed using the MTS assay (FIG. 17B). These results indicate that an increased SHP-1 activity was associated with decreased HSC proliferation.

4.7 1-[4-chloro-3-(trifluoromethyl)phenyl]-3-[3-(4-cyanophenoxy)phenyl]urea Activates SHP-1 by Interacting with its Inhibitory N—SH₂ Domain Next, we examined the effects of 1-[4-chloro-3-(trifluoromethyl)-phenyl]-3-[3-(4-cyanophenoxy)phenyl]urea-induced SHP-1 activity on the ectopic expression of different SHP-1 mutants. The 1-[4-chloro-3-(trifluoromethyl)phenyl]-3-[3-(4-cyanophenoxy)phenyl]urea treatment significantly increased the SHP-1 activity in the ectopic expression of the vector and wild-type SHP-1 but not in the ectopic expression of dN1 and D61A (FIG. 17C). Because 1-[4-chloro-3-(trifluoromethyl)]-3-[3-(4-cyanophenoxy)phenyl]urea treatment increased the SHP-1 activity, we further investigated the phenotypic change (cell apoptosis) and p-STAT3 expression in the ectopic expression of SHP-1 mutants after 1-[4-chloro-3-(trifluoromethyl)phenyl]-3-[3-(4-cyanophenoxy)phenyl]urea treatment. Considering the ectopic expression of the vector control and wild-type SHP-1, the 1-[4-chloro-3-(trifluoromethyl)phenyl]-3-[3-(4-cyanophenoxy)phenyl]urea treatment significantly increased the apoptotic LX2 cells and downregulated p-STAT3 (FIG. 17D and FIG. 17E). However, the dN1 and D61A mutants were insensitive to 1-[4-chloro-3-(trifluoromethyl)phenyl]-3-[3-(4-cyanophenoxy)phenyl]urea treatment considering cell apoptosis and p-STAT3 downregulation (FIG. 17E), indicating that 1-[4-chloro-3-(trifluoromethyl)phenyl]-3-[3-(4-cyanophenoxy)phenyl]urea could not interact with the dN1 and D61A mutants to activate the SHP-1 activity.

These results suggested that the ectopic expression of SHP-1, dN1, and D61A significantly inhibit cell proliferation. The D61 site of the inhibitory N—SH₂ domain was crucial for 1-[4-chloro-3-(trifluoromethyl)phenyl]-3-[3-(4-cyanophenoxy)phenyl]urea-induced SHP-1 upregulation. The overexpression of the dN1 and D61A mutants abolished the 1-[4-chloro-3-(trifluoromethyl)phenyl]-3-[3-(4-cyanophenoxy)phenyl]urea-induced SHP-1 activation, cell apoptosis, and p-STAT3 downregulation. The anti-fibrotic mechanism of 1-[4-chloro-3-(trifluoromethyl)phenyl]-3-[3-(4-cyanophenoxy)phenyl]urea in the SHP-1-STAT3 pathway was summarized in FIG. 17F.

Therefore, we demonstrated the SHP-1 overexpression in fibrotic areas of both human and mouse livers. 1-[4-chloro-3-(trifluoromethyl)phenyl]-3-[3-(4-cyanophenoxy)phenyl]urea exhibited an anti-fibrotic activity both in hepatotoxic and cholestatic fibrosis mouse models. We further illustrated that 1-[4-chloro-3-(trifluoromethyl)phenyl]-3-[3-(4-cyanophenoxy)phenyl]urea induced HSC apoptosis through its key anti-fibrotic mechanism. The SHP-1/STAT3 pathway was demonstrated as crucial in fibrogenesis and was involved in HSC survival. Through an interaction with the inhibitory N—SH₂ domain of SHP-1, 1-[4-chloro-3-(trifluoromethyl)phenyl]-3-[3-(4-cyanophenoxy)phenyl]urea increased the SHP-1 activity and downregulated p-STAT3, and was independent of PDGFR signaling.

The anti-fibrotic activity of 1-[4-chloro-3-(trifluoromethyl)phenyl]-3-[3-(4-cyanophenoxy)phenyl]urea was well demonstrated in different animal models. In addition, compared with the control, the 1-[4-chloro-3-(trifluoromethyl)phenyl]-3-[3-(4-cyanophenoxy)phenyl]urea treatment improved the survival of fibrotic mice. Notably, we observed cirrhosis regression after withdrawing the causative agent CCl₄. This finding was consistent with previous studies reporting that fibrosis may reverse after withdrawing the toxic agent and similar to a recent clinical finding that sustained viral suppression by antiviral therapy can regress cirrhosis in patients with CHB. Even in the process of fibrosis regression, the 1-[4-chloro-3-(trifluoromethyl)phenyl]-3-[3-(4-cyanophenoxy)phenyl]urea treatment significantly reduced the fibrosis, indicating that HSC apoptosis during the fibrosis resolution stage was crucial.

In conclusion, the results of the present invention suggest the relevance of the SHP-1/STAT3 pathway in fibrogenesis. 1-[4-chloro-3-(trifluoromethyl)phenyl]-3-[3-(4-cyanophenoxy)phenyl]urea activates SHP-1 through the direct interaction of the inhibitory N—SH₂ domain and promotes HSC apoptosis through the anti-fibrotic activity. Furthermore, 1-[4-chloro-3-(trifluoromethyl)phenyl]-3-[3-(4-cyanophenoxy)-phenyl]urea exhibited an anti-fibrotic activity in both hepatotoxic and cholestatic fibrosis mouse models. The SHP-1/STAT3 signaling pathway is a key in fibrogenesis. 1-[4-chloro-3-(trifluoromethyl)phenyl]-3-[3-(4-cyanophenoxy)phenyl]urea promotes up-regulation of SHP-1 activity and inhibits STAT3 phosphorylation to significantly improve fibrosis.

What is claimed is:

1. A method of ameliorating a fibrotic disease, comprising:
    administering to a subject in need thereof a therapeutically effective amount of 1-[4-chloro-3-(trifluoromethyl)phenyl]-3-[3-(4-cyanophenoxy)phenyl]urea represented by the structure shown below:

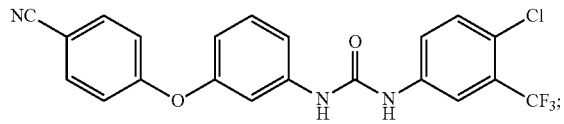 [SMILES: N#Cc1ccc(Oc2cccc(NC(=O)Nc3ccc(Cl)c(C(F)(F)F)c3)c2)cc1]

wherein the fibrotic disease is pulmonary fibrosis or hepatic fibrosis.

2. A method of treating a disease characterized by the inactivation of the SRC homology region 2-containing tyrosine phosphatase-1, comprising:
    administering to a subject in need thereof a therapeutically effective amount of a compound which is represented by the structure shown below:

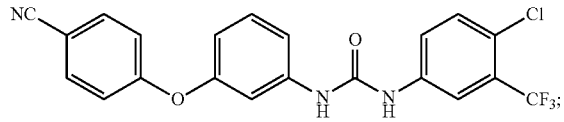 [SMILES: N#Cc1ccc(Oc2cccc(NC(=O)Nc3ccc(Cl)c(C(F)(F)F)c3)c2)cc1]

wherein the disease characterized by the inactivation of the SRC homology region 2-containing tyrosine phosphatase-1 is a fibrotic disease, and the fibrotic disease is pulmonary fibrosis or hepatic fibrosis.

* * * * *